United States Patent
Sokolova et al.

(10) Patent No.: US 9,994,908 B2
(45) Date of Patent: *Jun. 12, 2018

(54) MATERIALS AND METHODS FOR ASSESSMENT OF COLORECTAL ADENOMA

(71) Applicant: ABBOTT MOLECULAR INC., Des Plaines, IL (US)

(72) Inventors: Irina Sokolova, Villa Park, IL (US); Minghao Song, Lisle, IL (US); Svetlana Sitailo, Brookfield, IL (US); Frank Policht, Niles, IL (US)

(73) Assignee: Abbott Molecular Inc., Des Plaines, IL (US)

( * ) Notice: Subject to any disclaimer, the term of this patent is extended or adjusted under 35 U.S.C. 154(b) by 80 days.

This patent is subject to a terminal disclaimer.

(21) Appl. No.: 14/207,682

(22) Filed: Mar. 13, 2014

(65) Prior Publication Data

US 2014/0272962 A1 Sep. 18, 2014

Related U.S. Application Data

(60) Provisional application No. 61/786,062, filed on Mar. 14, 2013.

(51) Int. Cl.
*C12Q 1/68* (2018.01)
*G01N 1/30* (2006.01)
*G01N 33/50* (2006.01)
*G01N 33/574* (2006.01)

(52) U.S. Cl.
CPC ......... *C12Q 1/6886* (2013.01); *C12Q 1/6806* (2013.01); *C12Q 1/6841* (2013.01); *G01N 1/30* (2013.01); *G01N 33/5091* (2013.01); *G01N 33/57419* (2013.01); *C12Q 2537/16* (2013.01); *C12Q 2600/106* (2013.01); *C12Q 2600/158* (2013.01); *G01N 2001/305* (2013.01)

(58) Field of Classification Search
None
See application file for complete search history.

(56) References Cited

U.S. PATENT DOCUMENTS

| | | | |
|---|---|---|---|
| 4,892,829 A | 1/1990 | Gazdar et al. | |
| 5,491,224 A | 2/1996 | Bittner et al. | |
| 5,532,108 A | 7/1996 | Vogelstein | |
| 5,702,886 A | 12/1997 | Vogelstein et al. | |
| 5,756,696 A | 5/1998 | Gray et al. | |
| 5,834,190 A | 11/1998 | Vogelstein et al. | |
| 6,235,883 B1 | 5/2001 | Jakobovits et al. | |
| 7,090,978 B2 | 8/2006 | Perucho et al. | |
| 7,479,370 B2 | 1/2009 | Coignet | |
| 7,635,570 B2 | 12/2009 | Siena et al. | |
| 2005/0252773 A1 | 11/2005 | McBride et al. | |
| 2009/0069194 A1 | 3/2009 | Ramakrishnan | |
| 2010/0304374 A1 | 12/2010 | Meijer et al. | |
| 2011/0097759 A1 | 4/2011 | Cowens et al. | |
| 2011/0236396 A1 | 9/2011 | Pinto et al. | |
| 2013/0034546 A1 | 2/2013 | Rava et al. | |

FOREIGN PATENT DOCUMENTS

| | | |
|---|---|---|
| JP | 2008-536493 | 9/2008 |
| JP | 2016-513462 | 5/2016 |
| WO | WO-9318186 A1 | 9/1993 |
| WO | WO-9617958 A1 | 6/1996 |
| WO | WO-9850433 A2 | 11/1998 |
| WO | 2004/084874 | 10/2004 |
| WO | WO-2006107854 A2 | 1/2007 |

OTHER PUBLICATIONS

Habermann J.K., et al., "Genomic Instability and Oncogene Amplifications in Colorectal Adenomas Predict Recurrence and Synchronous Carcinoma," Modern Pathology, 2011, vol. 24 (4), pp. 542-555.
International Search Report and Written Opinion for Application No. PCT/US2014/025150, dated Jul. 3, 2014, 12 pages.
Andy Choo K.H., ed., In Situ Hibridization Protocols: Methods in Molecular Biology, vol. 33, Humana Press Inc., 1994, Table of Contents.
Bronner M.P., et al., "Genomic Biomarkers to Improve Ulcerative Colitis Neoplasia Surveillance," The American Journal of Pathology, 2008, vol. 173 (6), pp. 1853-1860.
Carter N.P., "Methods and Strategies for Analyzing Copy Number Variation Using DNA Microarrays," Nature Genetics, 2007, vol. 39 (Suppl. 7), pp. S16-S21.
Di Pietro M., et al., "Defective DNA Mismatch Repair Determines a Characteristic Transcriptional Profile in Proximal Colon Cancers," Gastroenterology, 2005, vol. 129 (3), pp. 1047-1059.
Fearon E.R., et al., "A Genetic Model for Colorectal Tumorigenesis," Cell, 1990, vol. 61 (5), pp. 759-767.
Gonzalez-González M., et al., "Prognostic Impact of Del(17p) and Del(22q) as Assessed by Interphase FISH in Sporadic Colorectal Carcinomas.," PLOS One, 2012, vol. 7 (8), pp. e42683.
Habermann J.K., et al., "Stage-Specific Alterations of the Genome, Transcriptome, and Proteome During Colorectal Carcinogenesis," Genes Chromosomes Cancer, 2007, vol. 46 (1), pp. 10-26.
Haddad B., et al., "Assignment1 of STAT1 to Human Chromosome 2q32 by FISH and Radiation Hybrids," Cytogenetics and Cell Genetics, 1998, vol. 83 (1-2), pp. 58-59.
Hermsen M., et al., "Colorectal Adenoma to Carcinoma Progression Follows Multiple Pathways of Chromosomal Instability," Gastroenterology, 2002, vol. 123 (4), pp. 1109-1119.
Herrick J., et al., "Quantifying Single Gene Copy Number by Measuring Fluorescent Probe Lengths on Combed Genomic DNA,"Proceedings of the National Academy of Sciences, 2000, vol. 97 (1), pp. 222-227.
Kallioniemi A., et al., "Comparative Genomic Hybridization for Molecular Cytogenetic Analysis of Solid Tumors," Science, 1992, vol. 258 (5083), pp. 818-821.
Kallioniemi O.P., et al., "ERBB2 Amplification in Breast Cancer Analyzed by Fluorescence in Situ Hybridization," Proceedings of the National Academy of Sciences, 1992, vol. 89 (12), pp. 5321-5325.
Kumar J., et al., "Detection of Differential Gene Copy Number Using Denaturing High Performance Liquid Chromatography," Journal of Biochemical and Biophysical Methods, 2005, vol. 64 (3), pp. 226-234.

(Continued)

Primary Examiner — Jehanne S Sitton
(74) Attorney, Agent, or Firm — Melissa E. Kolom; Casimir Jones, S.C.

(57) ABSTRACT

Methods of assessing colorectal adenoma, probes, and a kit.

6 Claims, 1 Drawing Sheet

(56) References Cited

OTHER PUBLICATIONS

Liu Z., et al., "Simple Copy Number Determination with Reference Query Pyrosequencing (RQPS)," Cold Spring Harbor Protocols, 2010, vol. 2010 (9), 10 pages.
Meijer G.A., et al., "Progression from Colorectal Adenoma to Carcinoma Is Associated with Non-Random Chromosomal Gains as Detected by Comparative Genomic Hybridisation," Journal of Clinical Pathology, 1998, vol. 51 (12), pp. 901-909.
Midgley R., et al., "Colorectal Cancer," Lancet, 1999, vol. 353 (9150), pp. 391-399.
Morrison, L.E. et al., "Labeling Fluorescence in Situ Hybridization Probes for Genomic Targets," Methods in Molecular Biology, 2002, vol. 204, pp. 21-40.
Munoz-Bellvis L., et al., "Unique Genetic Profile of Sporadic Colorectal Cancer liver Metastasis Versus Primary Tumors as Defined by High-density Single-nucleotide Polymorphism Arrays.," Modern Pathology, 2012, vol. 25 (4), pp. 590-601.
Pinkel D., et al., "Fluorescence in Situ Hybridization with Human Chromosome-Specific Libraries: Detection of Trisomy 21 and Translocations of Chromosome 4," Proceedings of the National Academy of Sciences, 1988, vol. 85 (23), pp. 9138-9142.
Rabinovitch P.S., et al., "Pancolonic Chromosomal Instability Precedes Dysplasia and Cancer in Ulcerative Colitis.," Cancer Research, 1999, vol. 59 (20), pp. 5148-5153.
Ried T., et al., "Comparative Genomic Hybridization Reveals a Specific Pattern of Chromosomal Gains and Losses During the Genesis of Colorectal Tumors," Genes Chromosomes Cancer, 1996, vol. 15 (4), pp. 234-246.
Rigby P.W., et al., "Labeling Deoxyribonucleic Acid to High Specific Activity in Vitro by Nick Translation with DNA Polymerase I," Journal of Molecular Biology, 1977, vol. 113 (1), pp. 113-237.
Sambrook J., et al., eds., Molecular Cloning: A Laboratory Manual, 3rd Edition, Cold Spring Harbor Laboratory, 2001, Table of Contents.
Sayagues J.M., et al., "Intratumoural Cytogenetic Heterogeneity of Sporadic Colorectal Carcinomas Suggests Several Pathways to Liver Metastasis.," The Journal of Pathology, 2010, vol. 221 (3), pp. 308-319.

Schouten J.P., et al., "Relative Quantification of 40 Nucleic Acid Sequences by Multiplex Ligation-dependent Probe Amplification," Nucleic Acids Research, 2002, vol. 30 (12), pp. e57.
Service R.F. "Gene Sequencing. The Race for the $1000 Genome," Science, 2006, vol. 311 (5767), pp. 1544-1546.
Shendure J., et al., "Advanced Sequencing Technologies: Methods and Goals," Nature Reviews. Genetics, 2004, vol. 5 (5), pp. 335-344.
Tijssen P., "Hybridization with Nucleic Acid Probes" in: Laboratory Techniques in Biochemistry and Molecular Biology, vol. 24, Chapter 2, Van der Vliet P.C., ed., Elsevier Publisher, 1993, pp. 19-78.
Vogelstein B., et al., "Digital PCR," Proceedings of the National Academy of Sciences, 1999, vol. 96 (16), pp. 9236-9241.
Varella-Garcia et al., "Multi-target interphase fluorescence in situ hybridization assay increases sensitivity of sputum cytology as a predictor of lung cancer," Cancer Detection and Prevention, 2004, 28: 244-251.
Comparative Genomic Hybridization [online], [retrieved on Feb. 2, 2017]. Retrieved from the Internet <URL: https://en.wikipedia.org/wiki/Comparative_genomic_hybridization#Limitations_of CGH_and_array_CGH>.
Sillars-Haderbol et al., "Identification of key genes for carcinogenic pathways associated with colorectal adenoma-to-carcinoma progression," Tumor Biol., 2010, vol. 31, pp. 89-96.
Simpson et al., "Intratumoral T cell infiltration, MHC class I and STAT1 as biomarkers of good prognosis in colorectal cancer," Gut, 2010, vol. 59, No. 7, pp. 926-933.
Roche, "Isolation of a Purified Epithelial Cell Population from Human Colon," Colorectal Cancer Methods and Protocols, Humana Press, 2001, pp. 15-20, ISBN: 978-089603-767-0.
Farrell et al., "High multidrug resistance (P-glycoprotein 170) expression in inflammatory bowel disease patients who fail medical therapy," Gastroenterology, 2000, vol. 118, pp. 279-288.
Rahman et al., "Cryopreservation of Cortical Tissue Blocks for the Generation of Highly Enriched Neuronal Cultures," Journal of Visualized Experiments, 2010, vol. 11, No. 45, #2384.
Komura et al., "Experimental Studies on Cryopreservation of Small Intestine in Rat," (Transplant), 1993, vol. 28, No. 2, pp. 189-199 (document showing well-known techniques).

MATERIALS AND METHODS FOR ASSESSMENT OF COLORECTAL ADENOMA

CROSS-REFERENCE TO RELATED APPLICATIONS

This application claims priority to U.S. provisional patent application No. 61/786,062, which was filed on Mar. 14, 2013, and which is hereby incorporated by reference in its entirety.

TECHNICAL FIELD

The present disclosure relates to methods of prognosis, including risk of progression, assessment of potential responsiveness to treatment with a therapeutic agent, monitoring of recurrence, and assessment of the efficacy of the therapeutic treatment of cancer, in particular colorectal adenocarcinoma, the detection of chromosomal abnormalities (e.g., changes in DNA copy number), a method of isolation of epithelial cells from fresh, fresh frozen or formalin-fixed, paraffin-embedded (FFPE) mammalian, e.g., human, tissue, and in situ hybridization, as well as a set of probes and a kit useful in such methods.

BACKGROUND

Colon cancer remains a leading cause of mortality worldwide, despite the well-characterized molecular events that occur during the progression from adenoma to carcinoma (Meijer et al., J. Clin. Pathol. 51: 901-909 (1998)). Colorectal carcinoma (CRC) is the third most common cancer and the second leading cause of cancer death in Europe and the United States, with 300,000 new cases and 200,000 deaths each year (Midgley et al., Lancet 353: 391-399 (1999)). Oncogenic transformation of colorectal epithelium to form invasive carcinomas is driven by the sequential acquisition of tumor-specific genetic aberrations and chromosomal aneuploidy (Fearon et al., Cell 61: 759-767 (1990); Ried et al., Genes Chromosomes Cancer 15: 234-245 (1996)).

A benign tumor of glandular origin, namely an adenoma, can become malignant over time, at which point it is referred to as an adenocarcinoma. Not all adenomas progress to adenocarcinomas. In fact, only a small subset of adenomas progress to adenocarcinomas.

Genomic instability is a key component of the progression from adenoma to adenocarcinoma. In about 15% of progressions there is a deficiency in the repair of DNA mismatch, which leads to microsatellite instability (designated MSI or MIN) (di Pietro et al., Gastroenterology 129: 1047-1059 (2005)). In the other 85% of progressions there is aneuploidy at the chromosomal level (designated CIN). It has now been well-established that changes in DNA copy number occur in specific patterns and are associated with different clinical behavior (Hermsen et al., Gastroenterology 123: 1109-1119 (2002)).

Chromosomal aberrations involving chromosomes 4, 5, 7, 8, 13, 15, 17, 18 and 20 have been frequently reported in CRC. Progression from adenoma to adenocarcinoma reportedly has been associated with 8p, 13q and 20q gains and 8p, 15q, 17p and 18q losses (Hermsen et al. (2002), supra). The most frequently observed chromosomal aberration in CRC is a gain of 20q, which reportedly occurs in more than 65% of CRC cases (Meijer et al. (1998), supra). Gains of 20q, in particular 20q12-q13, reportedly have been associated with poor outcome in CRC.

Sienna et al. (U.S. Pat. No. 7,635,570 B2, which issued Dec. 22, 2009) disclose the determination of the copy number of the epidermal growth factor receptor (EGFR) gene by fluorescent in situ hybridization (FISH) and quantitative polymerase chain reaction (PCR) on CRC samples. The method is disclosed to be useful for predicting whether an agent that binds EGFR will be efficacious in treating CRC, such as when there is an increase in the copy number of the EGFR gene. The method is also disclosed to be useful for assessing the efficacy of treatment of CRC, wherein a decrease in the copy number of the EGFR gene after treatment indicates that the treatment is effective. Sienna et al. discloses conflicting reports in the art about whether or not over-expression of EGFR can be correlated with prognosis of carcinoma.

Perucho et al. (U.S. Pat. No. 7,090,978 B2, which issued Aug. 15, 2006) disclose the detection of mutations, specifically insertions and deletions, by arbitrarily primed PCR (AP-PCR) to identify tumors, such as colon carcinoma. Vogelstein et al. (U.S. Pat. No. 5,532,108, which issued Jul. 2, 1996, U.S. Pat. No. 5,702,886, which issued Dec. 30, 1997, and U.S. Pat. No. 5,834,190, which issued Nov. 10, 1998) disclose the determination of chromosome 18q loss in the prognosis of patients with TNM (staging system developed by Union Internationale Centre Cancer (UICC) in which T represents primary tumor, N represents regional lymph node involvement, and M represents metastases) stage II and stage III colorectal cancer. Polymorphic genetic markers, such as on chromosome 18q, are amplified from standard formalin-fixed, paraffin-embedded tumor tissue. Vogelstein et al. specifically identifies the DCC (Deleted in Colorectal Carcinomas) gene.

Coignet et al. (U.S. Pat. No. 7,479,370 B2, which issued Jan. 20, 2009) disclose a method of detecting deletions in 13q14 in isolated lymphocytes. The deletions are reportedly associated with acute lymphoblastic leukemia (ALL) and chronic lymphocytic leukemia (CLL).

Gazdar et al. (U.S. Pat. No. 4,892,829, which issued Jan. 9, 1990) disclose a human plasma cell line. The cell line has a rearranged c-myc proto-oncogene (8q24).

Microarray-based gene expression profiling (Habermann et al., Genes Chromosomes & Cancer 46 (1): 10-26 (2007)) and comparative genomic hybridization (CGH) (Meijer et al. (1998), supra; and Hermsen et al., Gastroenterology 123: 1109-1119 (2002)) have been reported to provide progression pathways from colorectal adenoma to carcinoma. More recently, microRNA (miRNA) analysis has been reported to demonstrate that increased expression of the miR-17-92 cluster occurs during progression from colorectal adenoma to adenocarcinoma, and that increased expression is associated with a DNA copy number gain of the miR17-92 locus on 13q31 and c-myc expression.

Rava et al. (U.S. Pat. App. Pub. No. US 2013/0034546 A1, published Feb. 7, 2013) discloses a method for determining copy number variation (CNV) of a sequence of interest in a test sample. The method involves computational analysis of sequence reads of nucleic acids in the test sample. The analysis involves comparison of the sequence reads to chromosomal segments of interest, such as segments known to contain one or more oncogenes and/or one or more tumor suppressor genes. Aneuploidies can comprise an amplification of one or more regions, such as 20q13, 19q12, 1q21-1q23, 8p11-8p12, and 17q12, and can comprise a gene, such as MYC, ERBB2, CCND1, FGFR1, FGFR2, HRAS, KRAS, MYB, MDM2, CCNE, KRAS, MET, ERBB1, CDK4, MYCB, AKT2, MDM2, and CDK4. The cancer can be colorectal cancer.

Cowens et al. (U.S. Pat. App. Pub. No. US 2011/0097759 A1, published Apr. 28, 2011) discloses a method of predicting the clinical outcome in a subject diagnosed with colorectal cancer. The method comprises determining evidence of the expression of one or more predictive RNA transcripts or their expression products.

Pinto Morais de Carvalho et al. (U.S. Pat. App. Pub. No. US 2011/0236396 A1, published Sep. 29, 2011) discloses methods and compositions for diagnosing colorectal adenocarcinoma associated with a chromosomal aberration on chromosome 20q or a predisposition for developing such an adenocarcinoma by determining the expression levels of a set of marker genes. The method comprises detecting in a sample elevated expression levels of at least the marker genes RNPC1 and TCFL5.

Meijer et al. (U.S. Pat. App. Pub. No. 2010/0304374 A1, published Dec. 2, 2010) discloses an in vitro method for detecting the presence of colorectal adenocarcinoma cells. The method comprises detecting in a test sample elevated expression of at least the marker genes NM_017495 and NM_006602, both of which occur on chromosome 20q. The method can further comprise detecting elevated expression of NM_018840, NM_003600, NM_018270, NM_007002, and NM_016397, all of which occur on chromosome 20q. The method can comprise detecting in a test sample elevated expression of various other combinations of marker genes, such as at least 12 of Table 1, at least one of Table 17, two or more of Table 2 (8p), one or more of Table 3 (8q), three or more of Table 4 (13q), one or more of Table 5 (15q), one or more of Table 6 (17p), three or more of Table 7 (18q), nine or more of Table 8 (20q), two or more of Table 9 (20q), or at least one of Table 2 (8p), Table 3 (8q), Table 4 (13), Table 5 (15q), Table 6 (17p), Table 7 (18q), and either of Table 8 or 9 (20q).

It is clinically important to identify the progression of colorectal adenoma to adenocarcinoma as early as possible, in order to allow early-stage treatment, desirably in the absence of surgical intervention. In view of the foregoing, it is an object of the present disclosure to provide materials and methods to prognosticate, e.g., assess risk of progression, of colorectal adenoma. The materials and related methods can be used to assess potential responsiveness to treatment with a therapeutic agent, thereby enabling selection of a therapeutic agent for targeted treatment, monitor recurrence, and assess efficacy of therapeutic treatment of colorectal adenocarcinoma. Other objects and advantages, as well as inventive features, will become apparent from the detailed description provided herein.

SUMMARY

A method of prognosticating colorectal adenoma in a patient is provided. The method comprises contacting a sample of a colorectal adenoma (such as a sample of cells, such as a sample of epithelial cells) obtained from the patient with detectably labeled probes comprising a locus-specific probe for EGFR (epidermal growth factor receptor), a locus-specific probe for DCC (deleted in colorectal carcinoma), a chromosome enumeration probe for chromosome 18 (CEP18), a locus-specific probe for 13q14 (band 14 on the q arm of chromosome 13), and a locus-specific probe for MYC (c-myc oncogene) under hybridization conditions and determining the presence or absence of chromosomal abnormalities.

No chromosomal abnormalities indicates a low risk of recurrence of colorectal adenoma and/or a low risk of progression of colorectal adenoma to colorectal adenocarcinoma. An increase in copy number of EGFR indicates an increased risk of recurrence of colorectal adenoma and/or an increased risk of progression of colorectal adenoma to colorectal adenocarcinoma. A decrease in copy number of DCC relative to CEP18 indicates an increased risk of recurrence of colorectal adenoma and/or an increased risk of progression of colorectal adenoma to colorectal adenocarcinoma. An increase in copy number of EGFR in further combination with a decrease in copy number of DCC relative to CEP18, an increase in copy number of 13q14, and an increase in copy number of MYC indicates a high risk of recurrence of colorectal adenoma and/or a high risk of progression of colorectal adenoma to colorectal adenocarcinoma.

The detectably labeled probes can further comprise one or more other locus-specific probes and/or centromeric probes (CEP), such as a locus-specific probe for STAT1 (signal transducer and activator of transcription 1) and/or a locus-specific probe for AURKA (aurora kinase A). An increase in copy number of STAT1 and/or an increase in copy number of AURKA indicate(s) an increased risk of recurrence of colorectal adenoma and/or an increased risk of progression of colorectal adenoma to colorectal adenocarcinoma.

The sample, such as a sample of cells, e.g., epithelial cells, can be, and preferably is, obtained from a colorectal adenoma that is fresh, frozen upon being obtained from the patient, or fixed with formalin and embedded in paraffin (FFPE) upon being obtained from the patient. Preferably, the epithelial cells are obtained from a colorectal adenoma in accordance with a method comprising:

(a) rinsing a fresh sample or a thawed, freshly frozen sample of a colorectal adenoma in Hank's buffer at room temperature, (b) soaking the rinsed sample in pre-warmed Hank's buffer containing 20 mM DTT and 5 mM EDTA at 37° C. for around five minutes, (c) transferring the rinsed and soaked sample to Hank's buffer containing 20 mM DTT (dithiothreitol), 5 mM $CaCl_2$, and 10% DMSO (dimethylsulfoxide), and mixing for about 5 seconds to about 10 seconds, (d) pelleting cells by centrifugation at about 1000×g for about 10 minutes, (e) discarding supernatant from (d) and re-suspending the pelleted cells in residual supernatant, and (f) placing resuspended cells from (e) in a solution, which contains from about 30 wt. % to about 60 wt. % methanol, from about 40 wt. % to about 70 wt. % water, a buffer, and a preservative and which is kept at room temperature overnight. The method can further comprise:

(g) transferring the cells from (f) to a cytology slide, (h) soaking the slide in 95% ethanol for about 15 minutes at room temperature, (i) soaking the slide in Carnoy's solution (3:1 methanol: acetic acid fixative) for 30 minutes at room temperature, and (j) drying the slide at room temperature.

The sample, such as a sample of cells, e.g., epithelial cells, can be, and preferably is, fixed on a cytology slide, such as in accordance with the above method, prior to being contacted with the set of detectably labeled probes. The presence of epithelial cells can be confirmed by contacting the cells with a labeled anti-CAM5.2 antibody.

Further provided is a set of probes. The set of probes comprises a locus-specific probe for EGFR, a locus-specific probe for DCC, a chromosome enumerator probe for chromosome 18 (CEP18), a locus-specific probe for 13q14, and a locus-specific probe for MYC. The set of probes can further comprise one or more other locus-specific probes and/or centromeric probes (CEP), such as a locus-specific probe for STAT1 and/or a locus-specific probe for AURKA.

Still further provided is a kit. The kit comprises (a) a set of probes that enables prognosis of colorectal adenoma in a patient and (b) instructions for prognosticating colorectal adenoma in a patient. The set of probes comprises a locus-specific probe for EGFR, a locus-specific probe for DCC, a chromosome enumerator probe for chromosome 18 (CEP18), a locus-specific probe for 13q14, and a locus-specific probe for MYC. The set of probes can further comprise one or more other locus-specific probes and/or centromeric probes (CEP), such as a locus-specific probe for STAT1 and/or a locus-specific probe for AURKA. The instructions comprise determining in a sample, such as a sample of cells, e.g., epithelial cells, obtained from a colorectal adenoma obtained from the patient the presence or absence of chromosomal abnormalities. No chromosomal abnormalities indicates a low risk of recurrence of colorectal adenoma and/or a low risk of progression of colorectal adenoma to colorectal adenocarcinoma, whereas an increase in copy number of EGFR indicates an increased risk of recurrence of colorectal adenoma and/or an increased risk of progression of colorectal adenoma to colorectal adenocarcinoma, a decrease in copy number of DCC relative to CEP18 indicates an increased risk of recurrence of colorectal adenoma and/or an increased risk of progression of colorectal adenoma to colorectal adenocarcinoma, and an increase in copy number of EGFR in further combination with a decrease in copy number of DCC relative to CEP18, an increase in copy number of 13q14, and an increase in copy number of MYC indicates a high risk of recurrence of colorectal adenoma and/or a high risk of progression of colorectal adenoma to colorectal adenocarcinoma. An increase in copy number of STAT1 and/or an increase in copy number of AURKA indicate(s) an increased risk of recurrence of colorectal adenoma and/or an increased risk of progression of colorectal adenoma to colorectal adenocarcinoma.

Even still further provided is a method of isolating epithelial cells from a sample of adenoma. The method comprises:

(a) rinsing a fresh sample or a thawed, freshly frozen sample of an adenoma in Hank's buffer at room temperature, (b) soaking the rinsed sample in pre-warmed Hank's buffer containing 20 mM DTT and 5 mM EDTA at 37° C. for around five minutes, (c) transferring the rinsed and soaked sample to Hank's buffer containing 20 mM DTT (dithiothreitol), 5 mM CaCl$_2$, and 10% DMSO (dimethylsulfoxide), and mixing for about 5 seconds to about 10 seconds, (d) pelleting cells by centrifugation at about 1000×g for about 10 minutes, (e) discarding supernatant from (d) and re-suspending the pelleted cells in residual supernatant, and (f) placing resuspended cells from (e) in a solution, which contains from about 30 wt. % to about 60 wt. % methanol, from about 40 wt. % to about 70 wt. % water, a buffer, and a preservative and which is kept at room temperature overnight. The method can further comprise:

(g) transferring the cells from (f) to a cytology slide, (h) soaking the slide in 95% ethanol for about 15 minutes at room temperature, (i) soaking the slide in Carnoy's solution (3:1 methanol: acetic acid fixative) for 30 minutes at room temperature, and (j) drying the slide at room temperature.

In view of the above method, also provided is a cytology slide. The slide comprises epithelial cells isolated from a sample of an adenoma in accordance with the above method. The slide can be, if desired, stored at −20° C. until use.

DETAILED DESCRIPTION

The present disclosure provides methods for the prognosis, including risk of progression, assessment of potential responsiveness to treatment with a therapeutic agent, monitoring of recurrence, and assessment of the efficacy of the therapeutic treatment of cancer, in particular colorectal adenocarcinoma, as well as a set of probes and a kit useful in such methods.

Terms

The following terms are relevant to the present disclosure:

"About" refers to approximately a +/−10% variation from the stated value. It is to be understood that such a variation is always included in any given value provided herein, whether or not specific reference is made to it.

"Adenoma" is a benign tumor of glandular origin. "Adenoma," "colon adenoma," "adenoma of the colon," and "colonic adenoma" may be used herein to refer to an adenoma in the colon, which is also referred to as an adenomatous polyp. An adenomatous polyp is commonly found by colonoscopy and is removed because it has a tendency to become malignant.

"Adenocarcinoma," "colon adenocarcinoma," carcinoma of the colon," and "colonic adenocarcinoma" may be used herein to refer to a malignant growth (i.e., cancer) in the colon.

"AURKA" is used herein to refer to the aurora kinase A gene located at q13 on human chromosome 20. The Entrez Gene and HGNC cytogenetic bands are 20q13, whereas the Ensembl cytogenetic band is 20q13.2. Aliases for AURKA include ARK1, BTAK, STK15, STK6, AIK, PPP1R47, STK7, serine/threonine kinase 6, Aurora 2, Aurora-related kinase 1, Aurora/IPL1-related kinase 1, breast tumor-amplified kinase, serine/threonine-protein kinase 15, serine/threonine-protein kinase 6, serine/threonine-protein kinase aurora-A, ARK-1, AURA, hARK1, AURORA2, AurA, serine/threonine kinase 15, aurora/IPL1-like kinase, breast-tumor-amplified kinase, IPL1-related kinase, protein phosphatase 1 regulatory subunit 47, serine/threonine protein kinase 15, AIRK1, AYK1, EC2.7.11.1, and IAK1. "AURKA" is also used herein to refer to a probe or a set of probes used to determine a chromosomal abnormality involving AURKA, such as an increase in copy number. A probe for detecting a parameter involving AURKA, such as the copy number of AURKA, a copy number ratio involving AURKA, or the percentage gain of AURKA, by in situ hybridization, such as FISH, preferably hybridizes to the q13 region of chromosome 20 (20q13), which comprises the AURKA gene. DNA reference sequences include, but are not limited to, NC_000020.10 and NT_011362.10.

"Biomarker," as defined by the National Institutes of Health, is "a characteristic that is objectively measured and evaluated as an indicator of normal biologic processes, pathogenic processes, or pharmacologic responses to a therapeutic intervention."

"Chromosome enumeration probe (CEP)" or "centromeric probe" is any probe that enables the number of specific chromosomes in a cell to be enumerated. A chromosome enumeration probe typically recognizes and binds to a region near to (referred to as "peri-centromeric") or at the centromere of a specific chromosome, typically a repetitive DNA sequence (e.g., alpha satellite DNA). The centromere of a chromosome is typically considered to represent that chromosome, since the centromere is required for faithful segregation during cell division. Deletion or amplification of a particular chromosomal region can be differentiated from loss or gain of the whole chromosome (aneusomy), within which it normally resides, by comparing the number of signals corresponding to the particular locus (copy number) to the number of signals corresponding to the centromere. One method for making this comparison is to divide the number of signals representing the locus by the number of signals representing the centromere. Ratios of less than one indicate relative loss or deletion of the locus and ratios greater than one indicate relative gain or amplification of the locus. Similarly, comparison can be made between two different loci on the same chromosome, for example on two different arms of the chromosome, to indicate imbalanced gains or losses within the chromosome. In lieu of a centromeric probe for a chromosome, one of skill in the art will recognize that a chromosomal arm probe may alternately be used to approximate whole chromosomal loss or gain. However, such probes are not as accurate at enumerating chromosomes, since the loss of signals for such probes may not always indicate a loss of the entire chromosome. Examples of chromosome enumeration probes include CEP® probes commercially available from Abbott Molecular, Inc., Des Plaines, Ill. (formerly Vysis, Inc., Downers Grove, Ill.).

"Copy number" is a measurement of DNA, whether of a single locus, one or more loci, or an entire genome. A "copy number" of two is "wild-type" in a human (because of diploidy, except for sex chromosomes). A "copy number" of other than two in a human (except for sex chromosomes) deviates from wild-type. Such deviations include amplifications, i.e., increases in copy numbers, and deletions, i.e., decreases in copy numbers and even the absence of copy numbers.

"DCC" is used herein to refer to the deleted in colorectal carcinoma gene located in the region q21 on human chromosome 18. The Entrez Gene cytogenetic band is 18q21.3, whereas the Ensembl cytogenetic band is 18q21.2 and the HGNC cytogenetic band is 18q21.1. Aliases include IGDCC1, colorectal cancer suppressor, immunoglobulin superfamily DCC subclass member 1, tumor suppressor protein DCC, CRC18, CRCR1, colorectal tumor suppressor, deleted in colorectal cancer protein, and netrin receptor DCC. "DCC" also may be used herein to refer to a probe or a set of probes that can be used to determine a chromosomal abnormality involving DCC, such as DCC copy number loss. A probe for detecting a parameter involving DCC, such as the copy number of DCC, a copy number ratio involving DCC, or the percentage gain of DCC, by in situ hybridization, such as FISH, preferably hybridizes to the q21 region of chromosome 18 (18q21), which comprises the DCC gene. DNA reference sequences include, but are not limited to, NC_000018.9 and NT_010966.14.

"EGFR" is used herein to refer to the epidermal growth factor receptor gene located in the region p12 on human chromosome 7. The Entrez Gene cytogenetic band and the HGNC cytogenetic band are 7p12, whereas the Ensembl cytogenetic band is 7p11.2. Aliases include avian erythroblastic leukemia viral (v-erb-b) oncogene homolog, ERBB, ERBB1, proto-oncogene c-ErbB-1, receptor tyrosine-protein kinase erbB-1, HER1, EC 2.7.10.1, PlG61, cell growth inhibiting protein 40, cell proliferation-inducing protein 61, mENA, and EC 2.7.10. "EGFR" also may be used herein to refer to a probe or a set of probes that can be used to determine a chromosomal abnormality involving EGFR, such as EGFR copy number gain. A probe for detecting a parameter involving EGFR, such as the copy number of EGFR, a copy number ratio involving EGFR, or the percentage gain of EGFR, by in situ hybridization, such as FISH, preferably hybridizes to the p12 region of chromosome 7 (7p12), which comprises the EGFR gene. DNA reference sequences include, but are not limited to, NC_000007.13, NT_033968.6, and NT_079592.2.

"Labeled," "labeled with a detectable label," and "detectably labeled" are used interchangeably herein to indicate that an entity (e.g., a probe) can be detected. "Label" and "detectable label" mean a moiety attached to an entity to render the entity detectable, such as a moiety attached to a probe to render the probe detectable upon binding to a target sequence. The moiety, itself, may not be detectable but may become detectable upon reaction with yet another moiety. Use of the term "detectably labeled" is intended to encompass such labeling. The detectable label can be selected such that the label generates a signal, which can be measured and the intensity of which is proportional to the amount of bound entity. A wide variety of systems for labeling and/or detecting molecules, such as nucleic acids, e.g., probes, are well-known. Labeled nucleic acids can be prepared by incorporating or conjugating a label that is directly or indirectly detectable by spectroscopic, photochemical, biochemical, immunochemical, electrical, optical, chemical, or other means. Suitable detectable labels include radioisotopes, fluorophores, chromophores, chemiluminescent agents, microparticles, enzymes, magnetic particles, electron dense particles, mass labels, spin labels, haptens, and the like. Fluorophores and chemiluminescent agents are preferred herein.

"Locus-specific probe" and "locus-specific identifier (LSI)" may be used interchangeably herein to refer to a probe that selectively binds to a specific locus in a region on a chromosome, e.g., a locus that has been determined to undergo gain/loss in metastasis. A probe can target coding or non-coding regions, or both, including exons, introns, and/or regulatory sequences, such as promoter sequences and the like.

"MYC" is used herein to refer to the c-myc oncogene located in the region of q24 on chromosome 8. The Entrez Gene and Ensembl cytogenetic bands are 8q24.21, whereas the HGNC cytogenetic band is 8q24. Aliases include vHLHe39, c-Myc, v-myc avian myelocytomatosis viral oncogene homolog, Class E basic helix-loop-helix protein 39, proto-oncogene c-Myc, transcription factor p64, MRTL, avian myelocytomatosis viral oncogene homolog, myc proto-oncogene protein, myc-related translation/localization regulatory factor, and BHLHE39. MYC also may be used herein to refer to a probe or a set of probes that can be used to determine a chromosomal abnormality involving MYC, such as MYC copy number gain. A probe for detecting a parameter involving MYC, such as the copy number of MYC, a copy number ratio involving MYC, or the percentage gain of MYC, by in situ hybridization, such as FISH, preferably hybridizes to the q24 region of chromosome 8 (8q24), which comprises the MYC gene. DNA reference sequences include, but are not limited to, NC_000008.10 and NT_008046.16.

"Nucleic acid sample" refers to a sample comprising nucleic acid in a form suitable for hybridization with a probe, such as a sample comprising nuclei or nucleic acids isolated or purified from such nuclei. The nucleic acid sample may comprise total or partial (e.g., particular chromosome(s)) genomic DNA, total or partial mRNA (e.g., particular chromosome(s) or gene(s)), or selected sequence(s). Condensed chromosomes (such as are present in interphase or metaphase) are suitable for use as targets in in situ hybridization, such as FISH.

"Predetermined cutoff" and "predetermined level" refer generally to a cutoff value that is used to assess diagnostic/prognostic/therapeutic efficacy results by comparing the assay results against the predetermined cutoff/level, where the predetermined cutoff/level already has been linked or associated with various clinical parameters (e.g., severity of disease, progression/nonprogression/improvement, etc.).

"Probe," in the context of the present disclosure, is an oligonucleotide or polynucleotide that can selectively hybridize to at least a portion of a target sequence under conditions that allow for or promote selective hybridization. In general, a probe can be complementary to the coding or sense (+) strand of DNA or complementary to the non-coding or anti-sense (−) strand of DNA (sometimes referred to as "reverse-complementary"). Probes can vary significantly in length. A length of about 10 to about 100 nucleotides, such as about 15 to about 75 nucleotides, e.g., about 15 to about 50 nucleotides, can be preferred in some applications, whereas a length of about 50-1×10$^5$ nucleotides can be preferred for chromosomal probes and a length of about 25,000 to about 800,000 nucleotides can be preferred for locus-specific probes.

"Prognosis" is a prediction of the probable course and/or outcome of a disease, such as the likelihood of recovery. Thus, prognosis encompasses an improvement in disease status, a worsening in disease status, and no change in disease status.

"RB1" is used herein to refer to the retinoblastoma gene located in the region of q14 on human chromosome 13. The Entrez, Ensembl, and HGNC cytogenetic bands are 13q14.2. Aliases include OSRC, RB, p105-Rb, pRb, pp110, osteosarcoma, retinoblastoma suspectibility protein, retinoblastoma-associated protein, and Rb. "RB1" may be used interchangeably herein with "13q14". "RB1" or "13q14" also may be used herein to refer to a probe or a set of probes that can be used to determine a chromosomal abnormality involving RB1 or 13q14, such as RB1 or 13q14 copy number gain. A probe for detecting a parameter involving RB1 or 13q14, such as the copy number of RB1 or 13q14, a copy number ratio involving RB1 or 13q14, or the percentage gain of RB1 or 13q14, by in situ hybridization, such as FISH, preferably hybridizes to the q14 region of chromosome 13 (13q14), which comprises the RB1 gene. DNA reference sequences include, but are not limited to, NC_000013.10 and NT_024524.14.

"Risk of progression" is used herein to refer to a worsening in disease status.

"Selectively hybridize to" (as well as "selective hybridization," "specifically hybridize to," and "specific hybridization"), in the context of the present disclosure, refers to the binding, duplexing, or hybridizing of a nucleic acid molecule preferentially to a particular nucleotide sequence under stringent conditions. The term "stringent conditions" refers to conditions under which a probe will hybridize preferentially to its target sequence, and to a lesser extent to, or not at all to, other non-target sequences. A "stringent hybridization" and "stringent hybridization wash conditions" in the context of nucleic acid hybridization (e.g., as in array, Southern hybridization, Northern hybridization, or FISH) are sequence-dependent, and differ under different conditions. An extensive guide to the hybridization of nucleic acids is found in, e.g., Tijssen, *Laboratory Techniques in Biochemistry and Molecular Biology—Hybridization with Nucleic Acid Probes*, Part I, Ch. 2, "Overview of principles of hybridization and the strategy of nucleic acid probe assays," Elsevier, N.Y. (1993). Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids, which have more than 100 complementary residues, on an array or on a filter in a Southern or Northern blot is 42° C. using standard hybridization solutions (see, e.g., Sambrook and Russell, *Molecular Cloning: A Laboratory Manual*, 3rd ed., Vol. 1-3, Cold Spring Harbor Laboratory, Cold Spring Harbor Press, NY (2001)).

"STAT1" is used herein to refer to the signal transducer and activator of transcription 1 gene located at q32 on human chromosome 2. The Entrez Gene and Ensembl cytogenetic bands are 2q32.3, whereas the HGNC cytogenetic band is 2q32.2-q32.3. Aliases for STAT1 include STAT-1, ISGF-3, STAT91, transcription factor ISGF-3 components p91/p84, CANDF7, and signal transducer and activator of transcription 1-α/β. "STAT1" is also used herein to refer to a probe or a set of probes used to determine a chromosomal abnormality involving STAT1, such as an increase in copy number. A probe for detecting a parameter involving STAT1, such as the copy number of STAT1, a copy number ratio involving STAT1, or the percentage gain of STAT1, by in situ hybridization, such as FISH, preferably hybridizes to the q32 region of chromosome 2 (2q32), which comprises the STAT1 gene. DNA reference sequences include, but are not limited to, NC_000002.11 and NT_005403.17.

"Target sequence," "target region," and "nucleic acid target" refer to a nucleotide sequence that resides at a specific chromosomal location whose loss and/or gain, for example, is being determined.

The terminology used herein is for the purpose of describing particular embodiments only and is not otherwise intended to be limiting.

Methods

A method of prognosticating colorectal adenoma in a patient is provided. The method comprises contacting a sample (such as a sample of cells, e.g., epithelial cells) of a colorectal adenoma obtained from the patient with detectably labeled probes comprising a locus-specific probe for EGFR (epidermal growth factor receptor), a locus-specific probe for DCC (deleted in colorectal carcinoma), chromosome enumeration probe for chromosome 18 (CEP18), a locus-specific probe for 13q14 (band 14 on the q arm of chromosome 13), and a locus-specific probe for MYC (c-myc oncogene) under hybridization conditions and determining the presence or absence of chromosomal abnormalities. The detectably labeled probes can further comprise one or more other locus-specific probes and/or centromeric probes (CEP), such as a locus-specific probe for STAT1 (signal transducer and activator of transcription 1) and/or a locus-specific probe for AURKA (aurora kinase A). No chromosomal abnormalities indicates a low risk of recurrence of colorectal adenoma and/or a low risk of progression of colorectal adenoma to colorectal adenocarcinoma, whereas an increase in copy number of EGFR indicates an increased risk of recurrence of colorectal adenoma and/or an increased risk of progression of colorectal adenoma to colorectal adenocarcinoma, a decrease in copy number of DCC relative to CEP18 indicates an increased risk of recurrence of colorectal adenoma and/or an increased risk of progression of colorectal adenoma to colorectal adenocarcinoma, and an increase in copy number of EGFR in further combination with a decrease in copy number of DCC relative to CEP18, an increase in copy number of 13q14, and an increase in copy number of MYC indicates a high risk of recurrence of colorectal adenoma and/or a high risk of progression of colorectal adenoma to colorectal adenocarcinoma. An increase in copy number of STAT1 and/or an increase in copy number of AURKA indicate(s) an increased risk of recurrence of colorectal adenoma and/or an increased risk of progression of colorectal adenoma to colorectal adenocarcinoma.

The sample, such as a sample of cells, e.g., epithelial cells, can be, and preferably is, obtained from a colorectal adenoma that is fresh, frozen upon being obtained from the patient, or fixed with formalin and embedded in paraffin (FFPE) upon being obtained from the patient. Preferably, the epithelial cells are obtained from a colorectal adenoma in accordance with a method comprising:

(a) rinsing a fresh sample or a thawed, freshly frozen sample of a colorectal adenoma in Hank's buffer at room temperature, (b) soaking the rinsed sample in pre-warmed Hank's buffer containing 20 mM DTT and 5 mM EDTA at 37° C. for around five minutes, (c) transferring the rinsed and soaked sample to Hank's buffer containing 20 mM DTT (dithiothreitol), 5 mM $CaCl_2$, and 10% DMSO (dimethylsulfoxide), and mixing for about 5 seconds to about 10 seconds, (d) pelleting cells by centrifugation at about 1000×g for about 10 minutes, (e) discarding supernatant from (d) and re-suspending the pelleted cells in residual supernatant, and (f) placing resuspended cells from (e) in a solution, which contains from about 30 wt. % to about 60 wt. % methanol, from about 40 wt. % to about 70 wt. % water, a buffer, and a preservative and which is kept at room temperature overnight. The method can further comprise:

(g) transferring the cells from (f) to a cytology slide, (h) soaking the slide in 95% ethanol for about 15 minutes at room temperature, (i) soaking the slide in Carnoy's solution (3:1 methanol: acetic acid fixative) for 30 minutes at room temperature, and (j) drying the slide at room temperature.

The sample, such as a sample of cells, e.g., epithelial cells, can be, and preferably is, fixed on a cytology slide, such as in accordance with the above method, prior to being contacted with the set of detectably labeled probes. The presence of epithelial cells can be confirmed by contacting the cells with a labeled anti-CAM5.2 antibody.

The above method can be carried out using any suitable detection method known in the art. Preferably, the above method is carried out using in situ hybridization, such as fluorescence in situ hybridization (FISH). Preferably, each probe is detectably labeled, and, when two or more probes are used simultaneously or sequentially on the same sample, preferably each probe is detectably labeled with a distinct label, such as a distinct fluorophore.

When the above methods are carried out by in situ hybridization, in which each probe is detectably labeled (and, when two or more probes are used simultaneously or sequentially on the same sample, distinctly labeled), such as by FISH, in which each probe is labeled (and, when two or more probes are used simultaneously or sequentially on the same sample, distinctly labeled) with a fluorophore, the methods can be carried out on a sample of cells, such as a sample of epithelial cells obtained from an adenoma, which is fresh (fresh cells can be cultured for 1-3 days and a blocker, such as Colcemid, can be added to the culture to block the cells in metaphase, during which chromosomes are highly condensed and can be visualized), frozen, or fixed (e.g., fixed in formalin and embedded in paraffin (FFPE)), treated (e.g., with RNase and pepsin) to increase accessibility of target nucleic acid (e.g., DNA) and reduce non-specific binding, and then subjected to hybridization with one or more probes, washing to remove any unbound probes, and detection of hybridized probes. For example, a frozen colon tissue sample can be thawed at room temperature, rinsed in Hank's buffer, and soaked in pre-warmed Hank's buffer with 20 mM DTT (dithiothreitol) and 5 mM EDTA (ethylene diamine tetra-acetic acid) at 37° C. for five minutes, after which the tissue can be transferred into a 10 mL Falcon tube with 2 mL of shaking solution (Hank's buffer with 20 mM DTT, 5 mM $CaCl_2$, 5 mM $MgCl_2$, and 10% DMSO (dimethyl sulfoxide) at 4° C.) and the tube can be vortexed for 5-10 seconds. Then the tissue can be removed, and the supernatant can be centrifuged at 1,000×g for 10 minutes to pellet cells as exemplified in Example 1 for transfer to ThinPrep vials containing PreservCyt solution (Hologic, Inc., Bedford, Mass.). Slides can then be prepared using a ThinPrep T-2000 processor (Hologic, Inc., Bedford, Mass.) in accordance with manufacturer's instructions. Slides can be placed in 2×SSC at 73° C. for two minutes, incubated with pepsin (0.5 mg/mL) at 37° C. for 10 minutes, placed in 1×PBS (phosphate-buffered saline) at room temperature for five minutes, 1% NBF (neutral-buffered formalin) at room temperature for five minutes, and 1×PBS at room temperature for five minutes. Slides can be dehydrated by placement in 70% ethanol, 85% ethanol, and 100% ethanol for one minute each and then air-dried. Probe and a coverslip can be applied, the coverslip sealed, and the slide co-denatured in ThermoBrite for two minutes at 72° C. and 12-18 hours (overnight) at 37° C. The next day slides can be treated with 0.4×SSC/0.3% NP-40 for two minutes at 73° C. and 2×SSC/0.1% NP-40 for one minute at room temperature and then air-dried, mounted with 4'6'-diamidino-2-phenylindole dihydrochloride hydrate (DAPI) I anti-fade solution (Abbott Molecular, Inc., Des Plaines, Ill.), and covered with a coverslip as exemplified in Example 2.

A section (approximately 5 μm in thickness) of a formalin-fixed, paraffin-embedded (FFPE) sample of adenoma cells can be mounted onto a slide, such as a SuperFrost Plus positively charged slide (available from ThermoShandon, Pittsburgh, Pa.), baked at 56° C. overnight, de-paraffinized, submerged in 1× saline sodium citrate, pH 6-9, at 80° C. for about 35 minutes, and washed in water for three minutes. After protease digestion (1-4 mg pepsin/mL in 0.1-0.2 N HCl) at 37° C. for 10-30 minutes, the section can be rinsed in water for three minutes, passed through graded ethanol, and dried.

Hybridization with one or more probes as described above using a FFPE section or slide with cell suspension (i.e., cytology slide) can be carried out at 37° C. for 16-18 hours in an automated co-denaturation instrument (HYBrite or ThermoBrite Denaturation/Hybridization System, Abbot Molecular, Inc., Des Plaines, Ill.) according to the manufacturer's instructions (such methods typically involve denaturation of probes and target nucleic acids). After hybridization, the section or cytology slide can be placed in washing buffer (2× saline sodium citrate/0.3% NP40; available from Abbott Molecular, Inc.) at room temperature for 2-10 minutes to remove the coverslip and then immersed in 73° C. washing buffer for two minutes, dried, and mounted with DAPI I anti-fade solution (Abbott Molecular, Inc.). Preferably, the slide is analyzed with an epi-fluorescence microscope equipped with single band-pass filters (Abbott Molecular, Inc.).

Prior to detection, cell samples may be optionally pre-selected based on apparent cytologic abnormalities. Pre-selection identifies suspicious cells, thereby allowing the screening to be focused on those cells. Pre-selection allows for faster screening and increases the likelihood that a positive result will not be missed. Cells from a biological sample can be placed on a microscope slide and visually scanned for cytologic abnormalities commonly associated with dysplastic and neoplastic cells. Such abnormalities include abnormalities in nuclear size, nuclear shape, and nuclear staining, as assessed by counterstaining nuclei with nucleic acid stains or dyes, such as propidium iodide or DAPI I, usually following hybridization of probes to their target DNAs. Typically, neoplastic cells harbor nuclei that are enlarged, irregular in shape, and/or show a mottled staining pattern. Propidium iodide, typically used at a concentration of about 0.4 µg/ml to about 5 µg/ml, is a red-fluorescing DNA-specific dye that can be observed at an emission peak wavelength of 614 nm. DAPI, typically used at a concentration of about 125 ng/ml to about 1,000 ng/ml, is a blue fluorescing DNA-specific stain that can be observed at an emission peak wavelength of 452 nm with a DAPI filter at low magnification. In this case, only those cells pre-selected for detection are subjected to counting for chromosomal losses and/or gains. Preferably, pre-selected cells on the order of at least 100, and preferably more when there appear to be many cells with abnormal nucleic using the DAPI filter, are chosen for assessing chromosomal losses and/or gains.

Alternatively, an area in a tissue evidencing some level of dysplasia or a suspicious lesion can be localized using the DAPI filter at low magnification and thoroughly inspected for the presence of nuclei harboring abnormal copy numbers of any probe. In a normal cell, two copies of a given probe will be detected. In an abnormal cell, more or less copies of a given probe will be detected. Areas with the most significant copy number changes are preferably selected for enumeration. Wherever possible, numerous abnormal areas are selected and, within each abnormal area, at least about 10 random nuclei are analyzed under high power (64× or 100× objective) so that at least about 100 nuclei are analyzed. Preferably, nuclei are non-overlapping and harbor sufficiently bright signals.

Alternatively, cells for detection may be chosen independent of cytologic or histologic features. For example, all non-overlapping cells in a given area or areas on a microscope slide may be assessed for chromosomal losses and/or gains. As a further example, cells on the slide, e.g., cells that show altered morphology, on the order of at least about 50, and more preferably at least about 100, in number that appear in consecutive order on a microscope slide may be chosen for assessing chromosomal losses and/or gains.

The copies of EGFR (7p12), DCC (18q21), CEP18, 13q14, and MYC (8q24) are counted. If one or more other locus-specific probes and/or centromeric probes (CEP) are used, such as a locus-specific probe for STAT1 and/or a locus-specific probe for AURKA, the copies of the respective locus/loci and/or chromosome(s) are also counted.

Thus, such methods comprise contacting a sample (such as cells, e.g., epithelial cells) of colorectal adenoma obtained from a patient, e.g., a nucleic acid sample, with detectably labeled probes comprising a locus-specific probe for EGFR (7p12), a locus-specific probe for DCC (18q21), a chromosome enumeration probe for chromosome 18 (CEP18), a locus-specific probe for 13q14, and a locus-specific probe for MYC (8p24) under conditions that allow (or promote) the probe to bind selectively with its target nucleic acid sequence and form a stable hybridization complex. The detectably labeled probes can further comprise one or more other locus-specific probes and/or centromeric probes (CEP), such as a locus-specific probe for STAT1 and/or a locus-specific probe for AURKA. Such methods further comprise detecting the formation of hybridization complexes and counting the number of hybridization complexes. If the detectably labeled probes further comprise one or more other locus-specific probes and/or centromeric probes (CEP), such as a locus-specific probe for STAT1 and/or a locus-specific probe for AURKA, the methods further comprise detecting the formation of hybridization complexes involving such additional probes and counting the number of hybridization complexes involving such additional probes. In view of the number of hybridization complexes comprising EGFR (7p12), DCC (18q21), CEP18, 13q14, and MYC (8q24), the method further comprises determining the copy number of EGFR (7p12), the copy number of DCC (18q21) relative to CEP18, the copy number of 13q14, and the copy number of MYC (8q24). In view of the number of hybridization complexes comprising one or more other locus-specific probes and/or centromeric probes (CEP), such as a locus-specific probe for STAT1 and/or a locus-specific probe for AURKA, the method further comprises determining the copy number of the respective locus/loci and/or chromosome(s), such as the copy number of STAT1 and/or the copy number of AURKA. If desired, the copy number can be compared to the expected or "normal" number of copies (i.e., 2 copies), wherein a copy number greater than 2 (i.e., for a gain) and a copy number less than 2 (i.e., for a loss) and/or relative loss compared based on a comparison of the copy number of an LSI probe and the copy number of a centromeric probe (also referred to herein as a chromosome enumeration probe (CEP)), as appropriate, indicates that the cell is abnormal by FISH. The presence of more than two copies of two or more loci is indicative of polysomy. An increase in copy number of a single locus, such as more than two copies of a single locus, is indicative of a single locus gain. While deparaffinization, pretreatment, staining, and routine slide washing also can be conducted in accordance with methods known in the art, use of an automated system, however, such as the VP 2000 Processor (Abbott Molecular, Inc., Des Plaines, Ill.), decreases the amount of time needed to prepare slides for evaluation. Slides can be prepared in large batches (e.g., 50 slides), as opposed to small batches (e.g., 4 slides) when standard Coplin jars are used for post-hybridization washing. In addition, the scoring of slides can be fully automated using automated imaging, thereby reducing the amount of hands-on time required for specimen analysis. Full automation also enables the use of an imaging algorithm that captures more abnormal cells more frequently and consistently. Also, while any suitable method of slide preparation known in the art can be used, slides are preferably prepared using ThinPrep 2000 (Hologic, Inc., Bedford, Mass.), which generates more uniform and consistent monolayers of cells.

Other methods already known in the art or currently under development may require or prefer the use of a sample, such as a sample of cells, e.g., epithelial cells, obtained from an adenoma, that is other than cells fixed in formalin and embedded in paraffin, e.g., fresh or frozen cells, homogenized cells, lysed cells, or isolated or purified nucleic acids (e.g., a "nucleic acid sample" such as DNA) from epithelial cells obtained from an adenoma ("sample of epithelial cells" as used herein is intended to encompass all forms of a sample of epithelial cells obtained from an adenoma, including nucleic acids isolated or purified from epithelial cells obtained from an adenoma, that enable the determination of copy number and gain/loss). Nuclei also can be extracted from thick sections of paraffin-embedded specimens to reduce truncation artifacts and eliminate extraneous embedded material. Typically, biological samples, once obtained, are harvested and processed prior to hybridization using standard methods known in the art. Such processing typically includes protease treatment and additional fixation in an aldehyde solution, such as formaldehyde.

Examples of methods that can be used herein include, but are not limited to, quantitative polymerase chain reaction (Q-PCR), real-time Q-PCR (Applied Biosystems, Foster City, Calif.), densitometric scanning of PCR products, digital PCR, optionally with pre-amplification of the gene(s) and/or chromosomal region(s) for which copy number(s) is/are to be determined (see, e.g., Vogelstein et al., PNAS USA 96: 9236-9241 (1999); U.S. Pat. App. Pub. No. 2005/0252773; and U.S. Pat. App. Pub. No. 2009/0069194), comparative genomic hybridization (CGH; see, e.g., Kallioniemi et al., Science 258: 818-821 (1992); and Int'l Pat. App. Pub. No. WO 93/18186), microsatellite or Southern allelotype analysis, dot blots, arrays, microarrays (Carter, Nature Genetics Supplement 39: S16-S21 (July 2007)), multiplex amplifiable probe hybridization (MAPH), multiplex ligation-dependent probe amplification (MLPA; see, e.g., Schouten et al., Nucleic Acids Res. 30: e 57 (2002)), denaturing high performance liquid chromatography (dHPLC; Kumar et al., J. Biochem. Biophys. Methods 64(3): 226-234 (2005)), dynamic allele-specific hybridization (DASH), measuring fluorescent probe lengths on combed genomic DNA (Herrick et al., PNAS 97(1): 222-227 (2000)), reference query pyrosequencing (RQPS; Liu et al., Cold Spring Harb. Protoc. doi: 10.1101/pdb.prot5491 (2010)), mapping of fosmid ends onto a reference sequence (capillary-based technology), microelectrophoretic and nanopore sequencing (see, e.g., Service, Science 311: 1544-1546 (2006); and Shendure et al., Nat. Rev. Genet. 5: 335-344 (2004)), and the like.

Denaturation of nucleic acid targets for analysis by in situ hybridization and similar methods typically is done in such a manner as to preserve cell morphology. For example, chromosomal DNA can be denatured by high pH, heat (e.g., temperatures from about 70-95° C.), organic solvents (e.g., formamide), and combinations thereof. Probes, on the other hand, can be denatured by heat in a matter of minutes.

After denaturation, hybridization is carried out. Conditions for specifically hybridizing the probes to their nucleic acid targets generally include the combinations of conditions that are employable in a given hybridization procedure to produce specific hybrids, the conditions of which may easily be determined by one of ordinary skill in the art. Such conditions typically involve controlled temperature, liquid phase, and contact between a probe and a target. Hybridization conditions vary depending upon many factors including probe concentration, target length, target and probe G-C content, solvent composition, temperature, and duration of incubation. At least one denaturation step can precede contact of the probes with the targets. Alternatively, the probe and the target can be subjected to denaturing conditions together while in contact with one another, or with subsequent contact of the probe with the biological sample. Hybridization can be achieved with subsequent incubation of the probe/sample in, for example, a liquid phase of about a 50:50 volume ratio mixture of 2-4×SSC and formamide, at a temperature in the range of about 25 to about 55° C. for a time that is illustratively in the range of about 0.5 to about 96 hours, or more preferably at a temperature of about 32 to about 40° C. for a time in the range of about 2 to about 16 hours. In order to increase specificity, a blocking agent, such as unlabeled blocking nucleic acid, as described in U.S. Pat. No. 5,756,696 (the contents of which are herein incorporated by reference in their entirety, and specifically for the description of the use of blocking nucleic acid), can be used. Other conditions can be readily employed for specifically hybridizing the probes to their nucleic acid targets present in the sample, as would be readily apparent to one of skill in the art. Hybridization protocols are described, for example, in Pinkel et al., PNAS USA 85: 9138-9142 (1988); In situ Hybridization Protocols, Methods in Molecular Biology, Vol. 33, Choo, ed., Humana Press, Totowa, N.J. (1994); and Kallioniemi et al., PNAS USA 89: 5321-5325 (1992).

Upon completion of a suitable incubation period, non-specific binding of chromosomal probes to sample DNA can be removed by a series of washes. Temperature and salt concentrations are suitably chosen for a desired stringency. The level of stringency required depends on the complexity of a specific probe sequence in relation to the genomic sequence, and can be determined by systematically hybridizing probes to samples of known genetic composition. In general, high stringency washes can be carried out at a temperature in the range of about 65 to about 80° C. with about 0.2× to about 2×SSC and about 0.1% to about 1% of a non-ionic detergent, such as Nonidet P-40 (NP40). If lower stringency washes are required, the washes can be carried out at a lower temperature with an increased concentration of salt.

When fluorophore-labeled probes or probe compositions are used, the detection method can involve fluorescence microscopy, flow cytometry, or other means for determining probe hybridization. Any suitable microscopic imaging method can be used in conjunction with the methods described herein for observing multiple fluorophores. In the case where fluorescence microscopy is employed, hybridized samples can be viewed under light suitable for excitation of each fluorophore and with the use of an appropriate filter or filters. Automated digital imaging systems, such as the MetaSystems, BioView or Applied Imaging systems, alternatively can be used, along with signal enumeration and data acquisition algorithms.

Depending on the method employed, a digital image analysis system can be used to facilitate the display of results and to improve the sensitivity of detecting small differences in fluorescence intensity. An exemplary system is QUIPS (an acronym for quantitative image processing system), which is an automated image analysis system based on a standard fluorescence microscope equipped with an automated stage, focus control and filter wheel (Ludl Electronic Products, Ltd., Hawthorne, N.Y.). The filter wheel is mounted in the fluorescence excitation path of the microscope for selection of the excitation wavelength. Special filters (Chroma Technology, Brattleboro, Vt.) in the dichroic block allow excitation of the multiple dyes without image registration shift. The microscope has two camera ports, one of which has an intensified CCD camera (Quantex Corp., Sunnyvale, Calif.) for sensitive high-speed video image display, which is used for finding interesting areas on a slide as well as for focusing. The other camera port has a cooled CCD camera (model 200 by Photometrics Ltd., Tucson, Ariz.), which is used for the actual image acquisition at high resolution and sensitivity. The cooled CCD camera is interfaced to a SUN 4/330 workstation (SUN Microsystems, Inc., Mountain View, Calif.) through a VME bus. The entire acquisition of multicolor images is controlled using an image processing software package SCIL-Image (Delft Centre for Image Processing, Delft, Netherlands).

In array CGH (aCGH) the probes are immobilized at distinct locations on a substrate and are not labeled (see, e.g., Int'l Pat. App. Pub. No. WO 96/17958). Instead, sample nucleic acids, which comprise target nucleic acid(s), are labeled. Either the sample nucleic acids are labeled prior to hybridization or the hybridization complexes are detectably labeled. In dual- or multi-color aCGH the probe array is simultaneously or sequentially hybridized to two or more collections of differently labeled target nucleic acids.

Thus, in addition to their use in the prognosis of colorectal adenoma, e.g., risk of progression, the above methods can be used in the assessment of potential responsiveness to treatment with a therapeutic agent, monitoring recurrence, and assessment of the efficacy of the prophylactic or therapeutic treatment of colorectal adenocarcinoma. Thus, the methods can aid in treatment decisions, such as the selection of a treatment agent for therapy or prophylaxis, the selection of active surveillance or therapy over surgery, and the decision to employ adjuvant treatment(s) including the selection thereof. If desired, the methods described herein can be used in conjunction with other tests, such as routine cytology, histology, antigen assay, nomogram, methylation, mutation, and the like. The methods also can be used to confirm results previously or simultaneously obtained with other prognostic methods.

For example, if, during the course of performing an above-described method of prognosticating colorectal adenoma in a patient, it is determined that an increased copy number of EGFR is present, the decision could be made to treat the patient with an anti-EGFR agent. For example, an anti-EGFR antibody, such as panitumumab (Vectibix), which is a human IgG2 monoclonal antibody (mAb) that binds to human EGFR and reportedly has been shown to block binding of epidermal growth factor (EGF) to EGFR, thereby blocking receptor signaling, and inhibiting tumor cell activation and proliferation (see, e.g., Int'l Pat. App. Pub. No. WO 98/50433 and U.S. Pat. No. 6,235,883), or cetuximab (Erbitux), which is a chimeric mAb approved for treatment of KRAS mutation-negative, EGFR-expressing, metastatic colorectal cancer, could be administered to the patient to inhibit the progression of adenoma to adenocarcinoma and/or inhibit the recurrence of adenoma. Additionally or alternatively, the decision could be made to perform a follow-up colonoscopy on the patient in about one year.

Similarly, if, during the course of performing an above-described method of prognosticating colorectal adenoma in a patient, it is determined that a decreased copy number of DCC is present, the decision could be made to treat the patient with an alternative therapy, such as an anti-cancer therapy that does not involve an anti-EGFR agent. Examples of such alternative therapies include, but are not limited to, fluorouracil, cisplatin, doxorubicin, and cyclophosphamide. Additionally or alternatively, the decision could be made to perform a follow-up colonoscopy on the patient in about one year.

Similarly, if adenoma is discovered during the course of performing a colonoscopy on the patient and the adenomatous polyp(s) is/are removed, an above-described method could be used to monitor the patient for recurrence of adenoma. Likewise, if, during the course of performing an above-described method of prognosticating colorectal adenoma in a patient, it is determined that the patient is at low risk of recurrence of adenoma, such as when it is determined that there are no chromosomal abnormalities, the decision could be made to perform a follow-up colonoscopy on the patient in about five years.

If, during the course of performing an above-described method of prognosticating colorectal adenoma in a patient, it is determined that increased copy numbers of EGFR, MYC, and 13q14 and a decreased copy number of DCC relative to CEP18 are present, the decision could be made to treat the patient with an anti-EGFR agent, such as penitumumab and/or cetuximab, alone or in combination with an alternative or adjuvant therapy, such as fluorouracil, cisplatin, doxorubicin, and/or cyclophosphamide. Additionally, the decision could be made to perform a follow-up colonoscopy on the patient in about six months. Also additionally or alternatively, an above-described method could be used to assess efficacy of treatment by periodically performing the method over time and comparing the results over time, such as from one point in time to a subsequent or prior point in time.

If an above-described method is used to assess efficacy of treatment of the patient from whom the test sample was obtained, the method optionally further comprises modifying the therapeutic/prophylactic treatment of the patient as needed to improve efficacy. The method can be adapted for use in an automated system or a semi-automated system.

Generally speaking, when monitoring disease progression and/or treatment, the chromosomal abnormality (presence or level) may be "unchanged," "favorable" (or "favorably altered"), or "unfavorable" (or "unfavorably altered"). "Elevated" or "increased" refers to a level of chromosomal abnormality in a sample of epithelial cells obtained from an adenoma from a patient that is higher than a normal or typical level or range, or is higher than another reference level or range (e.g., earlier or baseline sample). The term "lowered" or "reduced" refers to a level of chromosomal abnormality in a sample of epithelial cells from an adenoma that is lower than a normal or typical level or range, or is lower than another reference level or range (e.g., earlier or baseline sample). The term "altered" refers to a level of chromosomal abnormality in a sample of epithelial cells from an adenoma that is altered (increased or decreased) over a normal or typical level or range, or over another reference level or range (e.g., earlier or baseline sample).

The normal or typical level or range for a given chromosomal abnormality is defined in accordance with standard practice. Because the levels of chromosomal abnormalities in some instances will be very low, a so-called altered level or alteration can be considered to have occurred when there is any net change as compared to the typical or normal level or range, or reference level or range, which cannot be explained by experimental error or sample variation. Thus, the level measured in a particular sample will be compared with the level or range of levels determined in similar samples from a so-called normal subject. In this context, a "normal subject" is an individual with no detectable disease, and a "normal" or "control" patient or population is/are one(s) that exhibit(s) no detectable disease, respectively, for example. Furthermore, given that chromosomal abnormalities are not routinely found at high levels in the majority of the human population, a "normal subject" can be considered an individual with no substantial detectable increased level of a given chromosomal abnormality, and a "normal" (sometimes termed "control") patient or population is/are one(s) that exhibit(s) no substantial detectable increased level of a given chromosomal abnormality. An "apparently normal subject" is one in which chromosomal abnormalities have not been or are being assessed. The level of a given chromosomal abnormality is said to be "elevated" when the chromosomal abnormality is normally undetectable, but is detected in a test sample, as well as when the analyte is present in the test sample at a higher than normal level.

The method can also involve the detection of other markers and the like.

Thus, when monitoring the efficacy of treatment of adenocarcinoma in a patient, the method can comprise the steps of:

(a) determining chromosomal abnormalities in a sample of epithelial cells from an adenocarcinoma from a subject prior to treatment with a therapeutic agent;

(b) determining the levels of chromosomal abnormalities in a later sample of epithelial cells from an adenocarcinoma from the subject after treatment with the therapeutic agent; and (c) comparing the levels of chromosomal abnormalities as determined in step (b) with the levels of chromosomal abnormalities as determined in step (a), wherein if the levels in step (b) are unchanged or unfavorable when compared to the levels determined in step (a), then adenocarcinoma is determined to have continued, progressed or worsened in the subject. By comparison, if the levels as determined in step (b) are favorable when compared to the levels as determined in step (a), then adenocarcinoma is likely to have discontinued, regressed or improved in the subject. Optionally, the method further comprises treating the subject, e.g., with one or more other therapeutic agents, radiation, and/or hormone therapy, for a period of time if the comparison shows that the levels as determined in step (b), for example, are unfavorably altered with respect to the levels determined in step (a). The period of time that the subject is treated can be determined by one skilled in the art (for example, the period of time can be from about seven (7) days to about two years, preferably from about fourteen (14) days to about one (1) year).

During the course of treatment, second and subsequent samples of adenocarcinoma cells are then obtained from the subject. The number of samples and the time in which said samples are obtained from the subject are not critical. For example, a second sample could be obtained seven (7) days after the subject is first treated, a third sample could be obtained two (2) weeks after the subject is first treated, a fourth sample could be obtained three (3) weeks after the subject is first treated, a fifth sample could be obtained four (4) weeks after the subject is first treated, etc.

After each second or subsequent sample is obtained from the subject, the levels of chromosomal abnormalities in the second or subsequent sample are determined (e.g., using the methods described herein or as known in the art). The levels as determined in each of the second and subsequent samples are then compared with the levels as determined in the first sample (e.g., the sample that was originally optionally compared to the predetermined level). If the levels as determined in step (c) are favorable when compared to the levels as determined in step (a), then adenocarcinoma cancer is likely to have discontinued, regressed or improved, and the subject should continue to be treated. However, if the levels determined in step (c) are unchanged or unfavorable when compared to the levels as determined in step (a), then adenocarcinoma is determined to have continued, progressed or worsened, and the subject should be treated with a higher dosage of pharmaceutical composition, radiation, or hormone, for example, or the subject should be treated differently.

Generally, for assays in which repeat testing may be done (e.g., monitoring disease progression and/or response to treatment), a second or subsequent test sample is obtained at a period in time after the first test sample has been obtained from the subject. Specifically, a second test sample from the subject can be obtained minutes, hours, days, weeks or years after the first test sample has been obtained from the subject. For example, the second test sample can be obtained from the subject at a time period of about 1 minute, about 5 minutes, about 10 minutes, about 15 minutes, about 30 minutes, about 45 minutes, about 60 minutes, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days, about 7 days, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years or about 10.0 years after the first test sample from the subject is obtained.

Moreover, the present disclosure also relates to methods of determining whether a subject predisposed to or suffering from adenoma or adenocarcinoma will benefit from treatment. In particular, the disclosure relates to companion diagnostic methods and products. Thus, the method of "monitoring the treatment of disease in a subject" as described herein further optimally also can encompass selecting or identifying candidates for therapy. Generally, the subject is one who has experienced some symptom of the disease or who has actually been diagnosed as having, or being at risk for, such a disease, and/or who demonstrates unfavorable levels of chromosomal abnormalities, as described herein.

The method optionally comprises an assay as described herein, where levels of chromosomal abnormalities are assessed before and following treatment of a subject. The observation of unfavorable levels of chromosomal abnormalities following treatment confirms that the subject will not benefit from receiving further or continued treatment, whereas the observation of favorable levels of chromosomal abnormalities following treatment confirms that the subject will benefit from receiving further or continued treatment. This confirmation assists with management of clinical studies, and provision of improved patient care.

Probes

A set of probes is also provided. The set of probes comprises, or consists of, a locus-specific probe for EGFR, a locus-specific probe for DCC, a chromosome enumeration probe for chromosome 18 (CEP18), a locus-specific probe for 13q14, and a locus-specific probe for MYC. The set of probes can further comprise, or consist of, a locus-specific probe for STAT1 and/or a locus-specific probe for AURKA.

An example of a probe for EGFR is Vysis LSI EGFR, which is available from Abbott Molecular, Inc., Des Plaines, Ill. The EGFR gene is ~188 kb. The probe extends beyond the gene for ~1 kb in the 5' direction and ~106 kb in the 3' direction. The entire probe is approximately 300 kb.

A probe for detecting a parameter involving EGFR by another method can be smaller, even substantially smaller, than the probe used for in situ hybridization, such as FISH, in which case the probe preferably hybridizes to a sequence within the EGFR gene (sequence information is available online from sources such as GenBank (www.ncbi.nlm.nih.gov/genbank) and GeneCards® (www.genecards.org)). "EGFR" is used herein to refer to any and all probes that can be used to determine a parameter involving EGFR, whether copy number, copy number ratio, percentage gain, and the like, irrespective of the particular method used to determine the parameter.

An example of a probe for DCC is Abnova DCC. Abnova DCC is manufactured by Abnova Corporation, Taiwan, and is distributed by Thermo Fisher Scientific Inc., Pittsburgh, Pa., under catalog number 89-028-963.

A probe for detecting a parameter involving DCC by another method can be smaller, even substantially smaller, than the probe used for in situ hybridization, such as FISH, in which case the probe preferably hybridizes to a sequence within the DCC gene (sequence information is available online from sources such as GenBank (www.ncbi.nlm.nih.gov/genbank) and GeneCards® (www.genecards.org)). "DCC" is used herein to refer to any and all probes that can be used to determine a parameter involving DCC, such as DCC relative to CEP18, whether copy number, copy number ratio, percentage gain, and the like, irrespective of the particular method used to determine the parameter.

An example of a probe for 13q14 or RB1 is Vysis LSI 13 (13q14), which is available from Abbott Molecular, Inc., Des Plaines, Ill. LSI 13 (13q14) consists of a set of overlapping clones that contain the RB 1 gene and flanking regions. The RB 1 gene is 180 kb. The probe extends beyond the gene for 110-170 kb in the 5' direction and approximately 120 kb in the 3' direction. The entire probe is approximately 440 kb in size and hybridizes to 7p11 region.

A probe for detecting a parameter involving 13q14 or RB1 by another method can be smaller, even substantially smaller, than the probe used for in situ hybridization, such as FISH, in which case the probe preferably hybridizes to a sequence within 13q14 or the RB1 gene (sequence information is available online from sources such as GenBank (www.ncbi.nlm.nih.gov/genbank) and GeneCards® (www.genecards.org)). "13q14 or RB1" is used herein to refer to any and all probes that can be used to determine a parameter involving 13q14 or RB1, whether copy number, copy number ratio, percentage gain, and the like, irrespective of the particular method used to determine the parameter.

An example of a probe for MYC is Vysis LSI MYC (8q24), which is available from Abbott Molecular, Inc., Des Plaines, Ill. The MYC gene is 4.4 kb. The probe extends beyond the gene for ~382 kb in the 5' direction and ~434 kb in the 3' direction. The entire probe is approximately 821 kb and hybridizes to the 8q24 region.

A probe for detecting a parameter involving MYC by another method can be smaller, even substantially smaller, than the probe used for in situ hybridization, such as FISH, in which case the probe preferably hybridizes to a sequence within the MYC gene (sequence information is available online from sources such as GenBank (www.ncbi.nlm.nih.gov/genbank) and GeneCards® (www.genecards.org)). "MYC" is used herein to refer to any and all probes that can be used to determine a parameter involving MYC, whether copy number, copy number ratio, percentage gain, and the like, irrespective of the particular method used to determine the parameter.

A probe for STAT1 can be prepared in accordance with methods known to those of ordinary skill in the art using sequence information available in the art. See, e.g., the reference sequence of Accession No. NG_008294.1, which is available from GenBank (www.ncbi.nlm.nih.gov/genbank), and Haddad et al., Cytogenet. Cell Genet. 83(1-2): 58-59 (1998), which is cited therein. Additional sequence information is also available by way of the BAC clone RP11-629B4, which is available from GenBank as Accession No. AC067945.4.

A probe for detecting a parameter involving STAT1 by another method can be smaller, even substantially smaller, than the probe used for in situ hybridization, such as FISH, in which case the probe preferably hybridizes to a sequence within the STAT1 gene (sequence information is available online from sources such as GenBank (www.ncbi.nlm.nih.gov/genbank) and GeneCards® (www.genecards.org)). "STAT1" is used herein to refer to any and all probes that can be used to determine a parameter involving STAT1, whether copy number, copy number ratio, percentage gain, and the like, irrespective of the particular method used to determine the parameter.

An example of a probe for AURKA is the Vysis AURKA FISH probe, which is available from Abbott Molecular, Inc., Des Plaines, Ill.

A probe for detecting a parameter involving AURKA by another method can be smaller, even substantially smaller, than the probe used for in situ hybridization, such as FISH, in which case the probe preferably hybridizes to a sequence within the AURKA gene (sequence information is available online from sources such as GenBank (www.ncbi.nlm.nih.gov/genbank) and GeneCards® (www.genecards.org)). "AURKA" is used herein to refer to any and all probes that can be used to determine a parameter involving AURKA, whether copy number, copy number ratio, percentage gain, and the like, irrespective of the particular method used to determine the parameter.

Suitable probes for use as chromosomal probes hybridize with repetitive DNA associated with the centromere of a chromosome. Centromeres of primate chromosomes contain a complex family of long-tandem repeats of DNA, which are composed of a monomer repeat length of about 171 base pairs (bp), that is referred to as α-satellite DNA. Chromosomal probes are typically about $50-1 \times 10^5$ nucleotides in length. Longer probes typically comprise smaller fragments of about 100-500 nucleotides in length.

Chromosome enumerator probes (CEP) and locus-specific probes that target a chromosome region or sub-region can be obtained commercially or readily prepared by those in the art. Such probes can be commercially obtained from Abbott Molecular, Inc. (Des Plaines, Ill.), Molecular Probes, Inc. (Eugene, Oreg.), or Cytocell (Oxfordshire, UK). Chromosomal probes can be prepared, for example, from protein nucleic acids (PNA), cloned human DNA such as plasmids, bacterial artificial chromosomes (BACs), and P1 artificial chromosomes (PACs) that contain inserts of human DNA sequences. A region of interest can be obtained via PCR amplification or cloning. In another embodiment, the chromosomal probes can be oligo probes. Alternatively, chromosomal probes can be prepared synthetically in accordance with methods known in the art.

When targeting of a particular gene locus is desired, probes that hybridize along the entire length of the targeted gene can be preferred, although not required. A locus-specific probe can be designed to hybridize to an oncogene or tumor suppressor gene, the genetic aberration of which is correlated with metastasis, e.g., MYC.

The probes can be prepared by any method known in the art. Probes can be synthesized or recombinantly produced. Such probes can range in length from about 25,000 base pairs to about 800,000 base pairs.

Preferably, probes are detectably labeled, and, when two or more probes are used simultaneously or sequentially on the same sample, preferably each probe is distinctly labeled. Preferably, the probes are detectably labeled with fluorophores. Examples of preferred fluorophores include, but are not limited to, 7-amino-4-methylcoumarin-3-acetic acid (AMCA), 5-carboxy-X-rhodamine, 6-carboxy-X-rhodamine, lissamine rhodamine B, 5-carboxyfluorescein, 6-carboxyfluorescein, fluorescein-5-isothiocyanate (FITC), 7-diethylaminocoumarin-3-carboxylic acid, tetramethylrhodamine-5-isothiocyanate, tetramethylrhodamine-6-isothiocyanate, 5-carboxyltetramethylrhodamine, 6-carboxytetramethylrhodamine, 7-hydroxycoumarin-3-carboxylic acid, N-4,4-difluoro-5,7-dimethy-4-bora-3a,4a-diaza-3-indacenepropionic acid, eosin-5-isothiocyanate, erythrosine-5-isothiocyanate, SpectrumRed™ (Abbott Molecular, Inc.), SpectrumGold™ (Abbott Molecular, Inc.), SpectrumGreen™ (Abbott Molecular, Inc.), SpectrumAqua™ (Abbott Molecular, Inc.), SpectrumOrange™ (Abbott Molecular, Inc., Des Plaines, Ill.), TEXAS RED (Molecular Probes, Inc.), Lucifer yellow, and CASCADE blue acetylazide (Molecular Probes, Inc.). The particular label used is not critical; desirably, however, the particular label does not interfere with in situ hybridization of the probe and the detection of label on any other probe. The label desirably is detectable in as low copy number as possible to maximize the sensitivity of the assay and be detectable above any background signal. Also desirably, the label provides a highly localized signal, thereby providing a high degree of spatial resolution.

Attachment of fluorophores to nucleic acid probes is well-known in the art and can be accomplished by any available means. Fluorophores can be covalently attached to a particular nucleotide, for example, and the labeled nucleotide incorporated into the probe using standard techniques such as nick translation, random priming (Rigby et al., J. Mol. Biol. 113: 237 (1997)), PCR labeling, end labeling, direct labeling by chemical modification of particular residues, such as cytosine residues (U.S. Pat. No. 5,491,224), and the like. Alternatively, the fluorophore can be covalently attached to nucleotides with activated linker arms, which have been incorporated into the probe, for example, via a linker to the deoxycytidine nucleotides of the probe that have been transaminated. Methods for labeling probes are described in U.S. Pat. No. 5,491,224, and Morrison et al., Molecular Cytogenetics: Protocols and Applications, Chapter 2, "Labeling Fluorescence In Situ Hybridization Probes for Genomic Targets," pp. 21-40, Fan, Ed., Humana Press (2002), both of which are herein incorporated by reference for their descriptions of labeling probes.

One of skill in the art will recognize that other agents or dyes can be used in lieu of fluorophores as label-containing moieties. Luminescent agents include, for example, radioluminescent, chemiluminescent, bioluminescent, and phosphorescent label-containing moieties. Agents that are detectable with visible light include cyanin dyes. Alternatively, detection moieties that are visualized by indirect means can be used. For example, probes can be labeled with biotin or digoxygenin using routine methods known in the art, and then further processed for detection. Visualization of a biotin-containing probe can be achieved via subsequent binding of avidin conjugated to a detectable marker. The detectable marker may be a fluorophore, in which case visualization and discrimination of probes can be achieved as described below.

Chromosomal probes hybridized to target regions alternatively can be visualized by enzymatic reactions of label moieties with suitable substrates for the production of insoluble color products. Each probe can be discriminated from other probes within the set by choice of a distinct label moiety. A biotin-containing probe within a set can be detected via subsequent incubation with avidin conjugated to alkaline phosphatase (AP) or horseradish peroxidase (HRP) and a suitable substrate. 5-bromo-4-chloro-3-indolylphosphate and nitro blue tetrazolium (NBT) serve as substrates for alkaline phosphatase, while diaminobenzoate serves as a substrate for HRP.

Kit

Also provided is a kit. The kit comprises (a) a set of probes that enables prognosis of colorectal adenoma in a patient and (b) instructions for prognosticating colorectal adenoma in a patient. Thus, the kit can comprise (a) a set of probes that enables prognosis of colorectal adenoma in a patient, wherein the set of probes comprises, or consists of, a locus-specific probe for EGFR, a locus-specific probe for DCC, chromosome enumeration probe for chromosome 18 (CEP18), a locus-specific probe for 13q14, and a locus-specific probe for MYC, and (b) instructions for prognosticating colorectal adenoma in a patient, wherein the instructions comprise determining in a sample (such as a sample of cells, e.g., epithelial cells) of a colorectal adenoma obtained from the patient the presence or absence of chromosomal abnormalities. The set of probes can further comprise one or more other locus-specific probes and/or centromeric probes (CEP), such as a locus-specific probe for STAT1 and/or a locus-specific probe for AURKA. No chromosomal abnormalities indicates a low risk of recurrence of colorectal adenoma and/or a low risk of progression of colorectal adenoma to colorectal adenocarcinoma, whereas an increase in copy number of EGFR indicates an increased risk of recurrence of colorectal adenoma and/or an increased risk of progression of colorectal adenoma to colorectal adenocarcinoma, a decrease in copy number of DCC relative to CEP18 indicates an increased risk of recurrence of colorectal adenoma and/or an increased risk of progression of colorectal adenoma to colorectal adenocarcinoma, and an increase in copy number of EGFR in further combination with a decrease in copy number of DCC relative to CEP18, an increase in copy number of 13q14, and an increase in copy number of MYC indicates a high risk of recurrence of colorectal adenoma and/or a high risk of progression of colorectal adenoma to colorectal adenocarcinoma. An increase in copy number of STAT1 and/or an increase in copy number of AURKA indicate(s) an increased risk of recurrence of colorectal adenoma and/or an increased risk of progression of colorectal adenoma to colorectal adenocarcinoma. Such kits may further comprise blocking agents or other probes, various labels or labeling agents to facilitate detection of the probes, reagents for hybridization (e.g., buffers), a metaphase spread, and the like.

Method of Isolating Epithelial Cells from an Adenoma

A method of isolating epithelial cells from a sample of an adenoma is also provided. The method comprises:

(a) rinsing a fresh sample or a thawed, freshly frozen sample of a colorectal adenoma in Hank's buffer at room temperature, (b) soaking the rinsed sample in pre-warmed Hank's buffer containing 20 mM DTT and 5 mM EDTA at 37° C. for around five minutes, (c) transferring the rinsed and soaked sample to Hank's buffer containing 20 mM DTT (dithiothreitol), 5 mM $CaCl_2$, and 10% DMSO (dimethylsulfoxide), and mixing for about 5 seconds to about 10 seconds, (d) pelleting cells by centrifugation at about 1000×g for about 10 minutes, (e) discarding supernatant from (d) and re-suspending the pelleted cells in residual supernatant, and (f) placing resuspended cells from (e) in a solution, which contains from about 30 wt. % to about 60 wt. % methanol, from about 40 wt. % to about 70 wt. % water, a buffer, and a preservative and which is kept at room temperature overnight. The method can further comprise:

(g) transferring the cells from (f) to a cytology slide, (h) soaking the slide in 95% ethanol for about 15 minutes at room temperature, (i) soaking the slide in Carnoy's solution (3:1 methanol:acetic acid fixative) for 30 minutes at room temperature, and (j) drying the slide at room temperature.

In view of the above method, also provided is a cytology slide. The slide comprises epithelial cells isolated from a sample of an adenoma in accordance with the above method. The slide can be, if desired, stored at −20° C. until use.

EXAMPLES

The following examples serve to illustrate the present disclosure. The examples are not intended to limit the scope of the claimed invention in any way.

Example 1

This example describes the isolation of epithelial cells from freshly frozen colon tissue samples and confirmation of the origin of the cells.

Frozen colon tissue samples were thawed at room temperature. The tissue was rinsed in Hank's buffer at room temperature. The tissue was then soaked in pre-warmed Hank's buffer with 20 mM DTT and 5 mM EDTA at 37° C. for five minutes. The tissue was transferred into a 10 mL Falcon tube with 2 mL of shaking solution (Hank's buffer with 20 mM DTT, 5 mM $CaCl_2$, 5 mM $MgCl_2$, and 10% DMSO at 4° C.), and the tube was vortexed for 5-10 seconds. The tissue was removed from the Falcon tube. The supernatant was centrifuged at 1,000×g for 10 minutes to spin down cells, after which the supernatant was discarded. Cells were re-suspended with residual supernatant. Cell suspensions from the first and second tubes were separately transferred into ThinPrep vials with 20 mL PreservCyt solution. The cells were fixed in PreservCyt solution overnight at room temperature. The vials were stored at ambient temperature until slide preparation. If the vials needed to be stored long-term, the vials were placed at 2-8° C.

Slides were made using a ThinPrep T-2000 processor in accordance with manufacturer's instructions. The slides were soaked in 95% ethanol for 15 minutes at room temperature and then immediately transferred into Carnoy's solution (3:1 methanol:acetic acid fixative) for 30 minutes at room temperature. Afterwards, the slides were dried in a vertical position at room temperature. If the slides needed to be stored long-term, the slides were stored at −20° C. until use.

The isolation of epithelial cells from tissue, such as fresh, fresh frozen, or formalin-fixed, paraffin-embedded (FFPE), was confirmed using an immunofluorescent anti-CAM5.2 antibody in accordance with the following procedure:

1. Rinse the slides with 1×PBS (phosphate-buffered saline).
2. Add 100 μL of 1% fresh Blocking Reagent (Invitrogen, Inc., Carlsbad, Calif.) prepared in PBS to the slides, and cover with Parafilm.
3. Incubate the slides in a humidified box at 37° C. for 25 minutes.
4. Remove the Parafilm, and discard the reagent off the slides by tapping.
5. Apply 100 μL of CAM5.2-FITC antibody to the slides, and cover with Parafilm.
6. Incubate the slides in a humidified box at 37° C. for 1 hour.
7. Wash the slides in 1×PBST (1×PBS with 0.05% Tween-20) at 37° C. for 5 minutes; repeat twice.
8. Apply DAPI and cover with coverslips.
9. View slides under regular fluorescent microscope with appropriate filters.

Microscopic evaluation revealed that >95% of the isolated cells was of epithelial origin.

Example 2

This example describes the fluorescence in situ hybridization (FISH) procedure used on the slides from Example 1.

Slides were placed in 2×SSC at 73° C. for two minutes, after which slides were incubated with pepsin (0.5 mg/mL) at 37° C. for 10 minutes. Subsequently, slides were placed in 1×PBS at room temperature for five minutes, 1% NBF at room temperature for five minutes, and 1×PBS at room temperature for five minutes. Slides were dehydrated by placement in 70% ethanol, 85% ethanol, and 100% ethanol for one minute each and then air dried. Probe (10 μl) and then a coverslip were applied to the slide. The cover-slip was sealed with rubber cement. Slides were co-denatured in ThermoBrite for two minutes at 72° C. and 12-18 hours (overnight) at 37° C. The next day slides were treated with 0.4×SSC/0.3% NP-40 for two minutes at 73° C. and 2×SSC/0.1% NP-40 for one minute at room temperature. Slides were then air dried, mounted with DAPI I anti-fade solution (Abbott Molecular, Inc., Des Plaines, Ill.) and covered with a coverslip.

Following hybridization, slides were evaluated using fluorescence microscopy with SpectrumGold™, SpectrumOrange™, SpectrumRed™, SpectrumGreen™, SpectrumAqua™, and DAPI filters. A cell was considered to be chromosomally abnormal if it possessed the following:

i.) gene copy number gain represented by three or more signals per cell, ii.) and/or gene copy number loss represented by one or zero signal, iii.) and/or the relative loss represented by the ratio of LSI probe to CEP probe being less than 1.0.

Fifty cells were enumerated in a designated target area on each slide, and the copy number of each probe was recorded.

Figure 1:
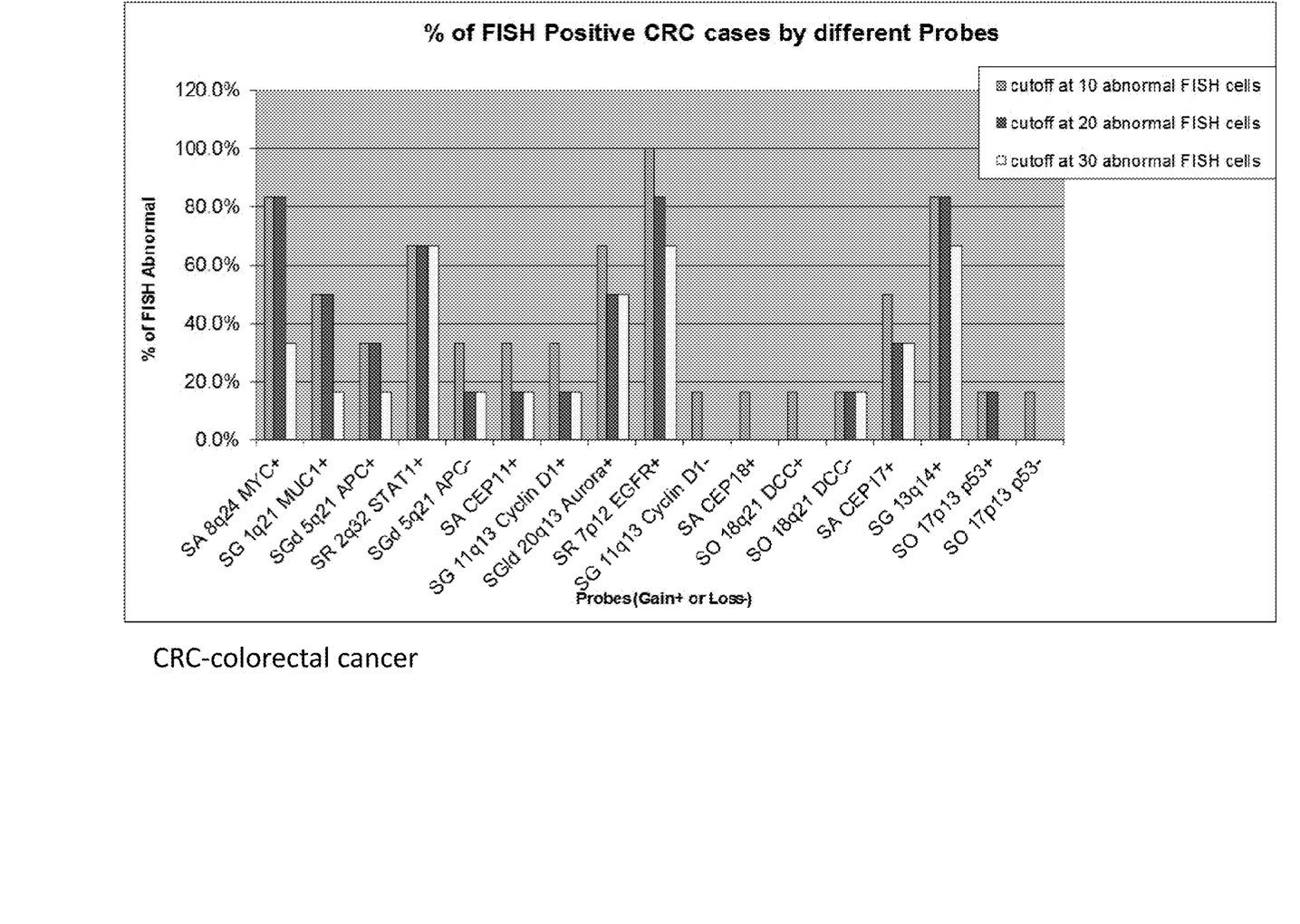
FIG. 1 is a graph of probes (gain (+) or loss (−)) vs. % FISH abnormal, which shows the percentage cases with the gene copy numbers changes for 13 probes detected in patient colon tumor samples, with cut-offs of 10, 20, and 30 abnormal cells.

Thirteen genomic regions associated with colorectal cancer (CRC) were evaluated on six CRC specimens and their respective normal adjacent tissues (NAT) to select FISH probes that had the highest frequency of chromosomal aberrations. The results are shown in FIG. 1, which is a graph of probes (gain (+) or loss (−)) vs. % FISH abnormal, which shows the percentage of cases with the gene copy numbers changes for 13 probes detected in patient colon tumor samples, with cut-offs of 10, 20, and 30 abnormal cells. Based on this assessment, five candidate probes (EGFR 7p12, MYC 8q24, 13q14, DCC 18q21, and CEP18) were selected for additional testing on a set of 27 frozen tissue specimens diagnosed with colorectal adenoma and 3 normal adjacent tissues. Of the 27 tested cases, 11 patients were diagnosed with concurrent colon cancer, whereas 16 patients with adenoma did not have concurrent colon cancer. For each specimen, FISH patterns were recorded for fifty cells/nuclei by one observer, and the number of chromosomally abnormal cells was evaluated. A cutoff point of at least 10 FISH abnormal cells was used to classify FISH positivity. A cell was considered as abnormal when it had copy number gains for EGFR, MYC and 13q14 probes and copy number loss for DCC relative to CEP18. The results showed that there were four distinct FISH patterns identified in colorectal adenoma cases: all four probes having no aberrations (disomic); only DCC gene loss; only EGFR gene gain; and all four probes abnormal, i.e., MYC, 13q14, and EGFR amplification and DCC deletion (see Table 1).

TABLE 1

|  | FISH negative | FISH positive | | |
| --- | --- | --- | --- | --- |
|  |  | DCC | EGFR | All FISH |
| Total Adenoma | all FISH | loss | gain | probes |
| (27) | probes normal | only | only | abnormal |
| Concurrent Cancer | 9.1% | 36.4% | 18.2% | 36.4% |
| (11) | (1/11) | (4/11) | (2/11) | (4/11) |
| No Concurrent | 62.5% | 0.0% | 18.8% | 18.8% |
| Cancer (16) | (10/16) | (0/16) | (3/16) | (3/16) |

In this limited set of samples, 91% of adenoma specimens obtained from patients with concurrent colorectal cancer were found to be FISH-positive, whereas only 38% of specimens were FISH-positive when obtained from patients who did not have concurrent colorectal cancer presented.

The observations suggest that different genetic profiles in adenoma specimens may have clinical value for personalized medicine. Patients with no FISH abnormalities (FISH pattern 1) may have the lowest risk of polyp recurrence and/or progression and have the best prognosis and, therefore, do not require treatment. For such patients, a follow-up colonoscopy, such as five years later, could be recommended. In contrast, patients with colonic adenomatous polyps abnormal for all probes (FISH pattern 4) could be at the highest risk of polyp recurrence and/or progression and, therefore, require treatment (e.g., anti-EGFR agent). For such patients, a follow-up colonoscopy, such as six months later, could be recommended. EGFR amplification (FISH pattern 2) may have an increased risk of polyp recurrence and/or progression and, therefore, could benefit from targeted drug therapy (e.g., anti-EGFR agent). For such patients, a follow-up colonoscopy, such as one year later, could be recommended. A unique group of patients with the sole aberration of the DCC gene loss (FISH pattern 3) may have an increased risk of polyp recurrence and/or progression and, therefore, could benefit from another therapy and may have poor prognosis. For such patients, a follow-up colonoscopy, such as one year later, could be recommended.

All patents, patent application publications, journal articles, textbooks, and other publications mentioned in the specification are indicative of the level of skill of those in the art to which the disclosure pertains. All such publications are incorporated herein by reference to the same extent as if each individual publication were specifically and individually indicated to be incorporated by reference.

The invention illustratively described herein may be suitably practiced in the absence of any element(s) or limitation(s), which is/are not specifically disclosed herein. Thus, for example, each instance herein of any of the terms "comprising," "consisting essentially of," and "consisting of" may be replaced with either of the other two terms. Likewise, the singular forms "a," "an," and "the" include plural references unless the context clearly dictates otherwise. Thus, for example, references to "the method" includes one or more methods and/or steps of the type, which are described herein and/or which will become apparent to those ordinarily skilled in the art upon reading the disclosure.

The terms and expressions, which have been employed, are used as terms of description and not of limitation. In this regard, where certain terms are set forth under "Terms" and are otherwise defined, described, explained, or discussed elsewhere in the "Detailed Description," all such definitions, descriptions, explanations, and discussions are intended to be attributed to such terms. There also is no intention in the use of such terms and expressions of excluding any equivalents of the features shown and described or portions thereof. Furthermore, while subheadings, e.g., "Terms," are used in the "Detailed Description," such use is solely for ease of reference and is not intended to limit any disclosure made in one section to that section only; rather, any disclosure made under one subheading is intended to constitute a disclosure under each and every other subheading.

It is recognized that various modifications are possible within the scope of the claimed invention. Thus, it should be understood that, although the present invention has been specifically disclosed in the context of preferred embodiments and optional features, those skilled in the art may resort to modifications and variations of the concepts disclosed herein. Such modifications and variations are considered to be within the scope of the invention as claimed herein.

What is claimed is:

1. A method of prognosticating colorectal adenoma in a patient, which method comprises:

contacting a sample of a colorectal adenoma obtained from the patient with a combination of detectably labeled probes under hybridization conditions, the combination consisting of a locus-specific probe for EGFR (epidermal growth factor receptor), a locus-specific probe for DCC (deleted in colorectal carcinoma), CEP18 (chromosome enumeration probe for chromosome 18), a locus-specific probe for 13q14 (band 14 on the q arm of chromosome 13), a locus-specific probe for MYC (c-myc oncogene), and optionally a locus-specific probe for STAT1 (signal transducer and activator of transcription 1) and/or a locus-specific probe for AURKA (aurora kinase A), and determining the presence or absence of chromosomal abnormalities, wherein no chromosomal abnormalities indicates a low risk of recurrence of colorectal adenoma and/or a low risk of progression of colorectal adenoma to colorectal adenocarcinoma, and wherein an increase in copy number of EGFR in further combination with a decrease in copy number of DCC relative to CEP18, an increase in copy number of 13q14, and an increase in copy number of MYC indicates a high risk of recurrence of colorectal adenoma and/or a high risk of progression of colorectal adenoma to colorectal adenocarcinoma, and wherein the sample of colorectal adenoma is a sample of epithelial cells obtained by a method comprising:

(a) rinsing a fresh sample or a thawed, freshly frozen sample of a colorectal adenoma in Hank's buffer at room temperature, (b) soaking the rinsed sample in pre-warmed Hank's buffer containing 20 mM DTT and 5 mM EDTA at 37° C. for five minutes, (c) transferring the rinsed and soaked sample to Hank's buffer containing 20 mM DTT (dithiothreitol), 5 mM CaC12, and 10% DMSO (dimethylsulfoxide), and mixing for about 5seconds to about 10 seconds, (d) pelleting cells by centrifugation at about 1000×g for about 10 minutes, (e) discarding supernatant from (d) and re-suspending the pelleted cells in residual supernatant, and (f) placing resuspended cells from (e) in a solution, which contains from about 30 wt. % to about 60 wt. % methanol, from about 40 wt. % to about 70 wt. % water, a buffer, and a preservative and which is kept at room temperature overnight, and whereupon colorectal adenoma in a patient is prognosticated.

2. The method of claim 1, wherein the sample of a colorectal adenoma is fresh from the patient, frozen upon being obtained from the patient, or fixed with formalin and embedded in paraffin (FFPE) upon being obtained from the patient.

3. The method of claim 1, which further comprises:
(g) transferring the cells from (f) to a cytology slide,
(h) soaking the slide in 95% ethanol for about 15 minutes at room temperature,
(i) soaking the slide in Carnoy's solution (3:1 methanol: acetic acid fixative) for 30 minutes at room temperature, and
(j) drying the slide at room temperature.

4. The method of claim 1, wherein the sample of a colorectal adenoma is fixed on a cytology slide prior to being contacted with the set of detectably labeled probes.

5. The method of claim 1, wherein the presence of epithelial cells in the sample of the colorectal adenoma is confirmed by contacting the cells with a labeled anti-CAM5.2 antibody.

6. A method of isolating epithelial cells from a sample of an adenoma and detecting a hybridized nucleic acid probe, which method comprises:

(a) rinsing a fresh sample or a thawed, freshly frozen sample of an adenoma in Hank's buffer at room temperature, (b) soaking the rinsed sample in pre-warmed Hank's buffer containing 20 mM DTT and 5 mM EDTA at 37° C. for around five minutes, (c) transferring the rinsed and soaked sample to Hank's buffer containing 20 mM DTT (dithiothreitol), 5 mM CaC12, and 10% DMSO (dimethylsulfoxide), and mixing for about 5seconds to about 10 seconds, (d) pelleting cells by centrifugation at about 1000×g for about 10 minutes, (e) discarding supernatant from (d) and re-suspending the pelleted cells in residual supernatant, (f) placing resuspended cells from (e) in a solution, which contains from about 30 wt. % to about 60 wt. % methanol, from about 40 wt. % to about 70 wt. % water, a buffer, and a preservative and which is kept at room temperature overnight, (g) transferring the cells from (f) to a cytology slide, (h) soaking the slide in 95% ethanol for about 15 minutes at room temperature.

(i) soaking the slide in Carnoy's solution (3:1 methanol: acetic acid fixative) for 30 minutes at room temperature.

(j) drying the slide at room temperature, and (k) subjecting the cells to a hybridization procedure comprising applying to the cells a combination of detectably labeled probes under hybridization conditions, the combination consisting of a locus-specific probe for EGFR (epidermal growth factor receptor), a locus-specific probe for DCC (deleted in colorectal carcinoma), CEP18 (chromosome enumeration probe for chromosome 18), a locus-specific probe for 13q14 (band 14 on the q arm of chromosome 13), a locus-specific probe for MYC (c-myc oncogene), and optionally a locus-specific probe for STAT1 (signal transducer and activator of transcription 1) and/or a locus-specific probe for AURKA (aurora kinase A).

* * * * *